(12) United States Patent
Vanoli et al.

(10) Patent No.: US 11,369,070 B2
(45) Date of Patent: Jun. 28, 2022

(54) LETTUCE VARIETIES 'DARK HORSE', 'HOTSHOT', AND 'UPPERCUT'

(71) Applicant: Pinnacle Seed, Inc., Carmel, CA (US)

(72) Inventors: Mike Vanoli, Carmel, CA (US); Michael Koda, Carmel, CA (US)

(73) Assignee: Pinnacle Seed, Inc., Carmel, CA (US)

( * ) Notice: Subject to any disclaimer, the term of this patent is extended or adjusted under 35 U.S.C. 154(b) by 0 days.

(21) Appl. No.: 17/029,864

(22) Filed: Sep. 23, 2020

(65) Prior Publication Data

US 2021/0084853 A1   Mar. 25, 2021

Related U.S. Application Data

(60) Provisional application No. 62/905,241, filed on Sep. 24, 2019.

(51) Int. Cl.
*A01H 6/14* (2018.01)
*A01H 5/12* (2018.01)

(52) U.S. Cl.
CPC ............ *A01H 6/1472* (2018.05); *A01H 5/12* (2013.01)

(58) Field of Classification Search
None
See application file for complete search history.

(56) References Cited

U.S. PATENT DOCUMENTS

| | | | |
|---|---|---|---|
| 8,362,326 B2 | 1/2013 | Bellec | |
| 8,389,810 B2 | 3/2013 | Ammerlaan | |
| 8,404,937 B2 | 3/2013 | Gibson | |
| 8,476,498 B2 | 7/2013 | Peng | |
| 8,772,578 B2 | 7/2014 | Ammerlaan | |
| 9,320,250 B2 | 4/2016 | Ammerlaan | |
| 9,814,210 B2 | 11/2017 | Ammerlaan et al. | |
| 10,123,502 B2 | 11/2018 | Vanoli | |
| 10,631,491 B2 | 4/2020 | Vanoli | |
| 10,785,937 B1 | 9/2020 | Vanoli | |
| 2012/0278955 A1* | 11/2012 | Gibson | ............ A01H 5/12 800/305 |
| 2012/0297496 A1 | 11/2012 | van der Laan | |
| 2017/0251622 A1 | 9/2017 | Sinclair et al. | |
| 2018/0249669 A1 | 9/2018 | Sinclair | |
| 2020/0288660 A1 | 9/2020 | Vanoli | |
| 2020/0375137 A1 | 12/2020 | Vanoli | |

OTHER PUBLICATIONS

Grant, A. (2018). "Different Lettuce Types: Varieties of Lettuce for the Garden," Obtained from <https://www.gardeningknowhow.com/edible/vegetables/lettuce/different-lettuce-types.htm>, 7 pages.

Liu et al., (1999). "First Report of Tomato Bushy Stunt Virus Isolated from Lettuce," Plant Disease, 83(3):301.

Mikel, M. (2013). "Genetic composition of contemporary proprietary U.S. lettuce (*Lactuca sativa* L.) cultivars," Genet Resour Crop Evol, 60:89-96.

(Continued)

*Primary Examiner* — Matthew R Keogh
*Assistant Examiner* — David R Byrnes
(74) *Attorney, Agent, or Firm* — Morrison & Foerster LLP

(57) ABSTRACT

New lettuce variety designated 'Hotshot' is described. 'Hotshot' exhibits stability and uniformity.

15 Claims, 88 Drawing Sheets

(88 of 88 Drawing Sheet(s) Filed in Color)

(56) References Cited

OTHER PUBLICATIONS

Nagata, R. T. (1992). "Clip and Wash Method of Emasculation for Lettuce." Hortscience 27(8):907-908.
Obermeier et al., (2001). "Characterization of Distinct Tombusviruses that Cause Diseases of Lettuce and Tomato in the Western United States." Phytopathology, 91(8):797-806.
Pinnacle Seed. Jun. 2019. 'Hotshot'. Product Sell Sheet. Available online at < http://pinnacleseed.net/sell-sheets/hotshot-sell-sheet.pdf>, Obtained on Sep. 18, 2020.1 page.
Pinnacle Seed. Jun. 2019. 'Uppercut'. Product Sell Sheet. Available online at < http://pinnacleseed.net/sell-sheets/PIN-021-Uppercut-sell-sheet-R1-20200310.pdf>, Obtained on Sep. 18, 2020.1 page.
Pinnacle Seed. Oct. 2018. 'Dark Horse'. Product Sell Sheet. Available online at <http://pinnacleseed.net/sell-sheets/PIN-021-sell-sheets-dark-horse-R2-20200421.pdf>, Obtained on Sep. 18, 2020.1 page.
Ryder et al., (1974). "Mist depollination of lettuce flowers." Hortscience, 9:584.
US Plant Variety Protection Certificate No. 200700432, Issued Mar. 12, 2012, Variety Showtime, Crop Name Lettuce, Applicant Harris Moran Seed Company, 79 pages.
US Plant Variety Protection Certificate No. 201000303, Issued Jun. 19, 2013, Variety Caretaker, Crop Name Lettuce, Applicant Harris Moran Seed Company, 28 pages.
US Plant Variety Protection Certificate No. 201100043, Issued Mar. 21, 2018, Variety Thunderhead, Crop Name Lettuce, Applicant 3 Star Lettuce, LLC, 34 pages.
US Plant Variety Protection Certificate No. 8900281, Issued Jun. 30, 1992, Variety Raider, Crop Name Lettuce, Applicant Genecorp, Inc., 17 pages.
US Plant Variety Protection Certificate No. 9800023, Issued Nov. 26, 2020, Variety Headmaster, Crop Name Lettuce, Applicant Progeny Advanced Genetics, Inc., 35 pages.
U.S. Unpublished U.S. Appl. No. 17/469,727, filed Sep 8, 2021, titled "Lettuce Variety '14RDSJV055-3'." (Copy not submitted herewith pursuant to the waiver of 37 C.F.R. § 1.98(a)(2)(iii)).

* cited by examiner

US 11,369,070 B2

LETTUCE VARIETIES 'DARK HORSE', 'HOTSHOT', AND 'UPPERCUT'

CROSS-REFERENCE TO RELATED APPLICATION

This application claims the benefit of U.S. Provisional Application No. 62/905,241, filed Sep. 24, 2019, which is hereby incorporated by reference in its entirety.

FIELD

This invention relates to the field of plant breeding. In particular, this invention relates to new lettuce, *Lactuca sativa*, varieties 'Dark Horse', 'Hotshot', and 'Uppercut'.

BACKGROUND

Lettuce is an increasingly popular crop. Worldwide lettuce consumption continues to increase. As a result of this demand, there is a continued need for new lettuce varieties. In particular, there is a need for improved lettuce varieties that are stable, high yielding, and agronomically sound.

SUMMARY

In order to meet these needs, the present invention is directed to improved lettuce varieties.

In one embodiment, the present invention is directed to lettuce, *Lactuca sativa*, seed designated as 'Dark Horse'. In one embodiment, the present invention is directed to a *Lactuca sativa* lettuce plant and parts isolated therefrom produced by growing 'Dark Horse' lettuce seed. In another embodiment, the present invention is directed to a *Lactuca sativa* plant and parts isolated therefrom having all the physiological and morphological characteristics of a *Lactuca sativa* plant produced by growing 'Dark Horse' lettuce seed. In still another embodiment, the present invention is directed to an $F_1$ hybrid *Lactuca sativa* lettuce seed, plants grown from the seed, and a head isolated therefrom having 'Dark Horse' as a parent, where 'Dark Horse' is grown from 'Dark Horse' lettuce seed.

Lettuce plant parts include lettuce heads, lettuce leaves, parts of lettuce leaves, pollen, ovules, flowers, and the like. In another embodiment, the present invention is further directed to lettuce heads, lettuce leaves, parts of lettuce leaves, flowers, pollen, and ovules isolated from 'Dark Horse' lettuce plants. In another embodiment, the present invention is further directed to tissue culture of 'Dark Horse' lettuce plants, and to lettuce plants regenerated from the tissue culture, where the plant has all of the morphological and physiological characteristics of 'Dark Horse' lettuce plants.

The present invention is further directed to a method of selecting lettuce plants by: a) growing more than one 'Dark Horse' lettuce plant, where the plants are grown from lettuce seed; and b) selecting a plant from step a). The present invention is further directed to lettuce plants and seeds produced therefrom, where the lettuce plants and seeds are isolated by the selection method of the invention.

In another embodiment, the present invention is further directed to a method of breeding lettuce plants by crossing a lettuce plant with a plant grown from 'Dark Horse' lettuce seed. In still another embodiment, the present invention is further directed to lettuce plants, lettuce parts from the lettuce plants (e.g., lettuce heads), and seeds produced therefrom where the lettuce plant is isolated by the breeding method of the invention.

In one embodiment, the present invention is directed to lettuce, *Lactuca sativa*, seed designated as 'Hotshot' having ATCC Accession Number PTA-127155. In one embodiment, the present invention is directed to a *Lactuca sativa* lettuce plant and parts isolated therefrom produced by growing 'Hotshot' lettuce seed. In another embodiment, the present invention is directed to a *Lactuca sativa* plant and parts isolated therefrom having all the physiological and morphological characteristics of a *Lactuca sativa* plant produced by growing 'Hotshot' lettuce seed having ATCC Accession Number PTA-127155. In still another embodiment, the present invention is directed to an $F_1$ hybrid *Lactuca sativa* lettuce seed, plants grown from the seed, and a head isolated therefrom having 'Hotshot' as a parent, where 'Hotshot' is grown from 'Hotshot' lettuce seed having ATCC Accession Number PTA-127155.

Lettuce plant parts include lettuce heads, lettuce leaves, parts of lettuce leaves, pollen, ovules, flowers, and the like. In another embodiment, the present invention is further directed to lettuce heads, lettuce leaves, parts of lettuce leaves, flowers, pollen, and ovules isolated from 'Hotshot' lettuce plants. In another embodiment, the present invention is further directed to tissue culture of 'Hotshot' lettuce plants, and to lettuce plants regenerated from the tissue culture, where the plant has all of the morphological and physiological characteristics of 'Hotshot' lettuce plants.

The present invention is further directed to a method of selecting lettuce plants by: a) growing more than one 'Hotshot' lettuce plant, where the plants are grown from lettuce seed having ATCC Accession Number PTA-127155; and b) selecting a plant from step a). The present invention is further directed to lettuce plants and seeds produced therefrom, where the lettuce plants and seeds are isolated by the selection method of the invention.

In another embodiment, the present invention is further directed to a method of breeding lettuce plants by crossing a lettuce plant with a plant grown from 'Hotshot' lettuce seed having ATCC Accession Number PTA-127155. In still another embodiment, the present invention is further directed to lettuce plants, lettuce parts from the lettuce plants (e.g., lettuce heads), and seeds produced therefrom where the lettuce plant is isolated by the breeding method of the invention.

In one embodiment, the present invention is directed to lettuce, *Lactuca sativa*, seed designated as 'Uppercut'. In one embodiment, the present invention is directed to a *Lactuca sativa* lettuce plant and parts isolated therefrom produced by growing 'Uppercut' lettuce seed. In another embodiment, the present invention is directed to a *Lactuca sativa* plant and parts isolated therefrom having all the physiological and morphological characteristics of a *Lactuca sativa* plant produced by growing 'Uppercut' lettuce seed. In still another embodiment, the present invention is directed to an $F_1$ hybrid *Lactuca sativa* lettuce seed, plants grown from the seed, and a head isolated therefrom having 'Uppercut' as a parent, where 'Uppercut' is grown from 'Uppercut' lettuce seed.

Lettuce plant parts include lettuce heads, lettuce leaves, parts of lettuce leaves, pollen, ovules, flowers, and the like. In another embodiment, the present invention is further directed to lettuce heads, lettuce leaves, parts of lettuce leaves, flowers, pollen, and ovules isolated from 'Uppercut' lettuce plants. In another embodiment, the present invention is further directed to tissue culture of 'Uppercut' lettuce plants, and to lettuce plants regenerated from the tissue culture, where the plant has all of the morphological and physiological characteristics of 'Uppercut' lettuce plants.

The present invention is further directed to a method of selecting lettuce plants by: a) growing more than one 'Uppercut' lettuce plant, where the plants are grown from lettuce seed; and b) selecting a plant from step a). The present invention is further directed to lettuce plants and seeds produced therefrom, where the lettuce plants and seeds are isolated by the selection method of the invention.

In another embodiment, the present invention is further directed to a method of breeding lettuce plants by crossing a lettuce plant with a plant grown from 'Uppercut' lettuce seed. In still another embodiment, the present invention is further directed to lettuce plants, lettuce parts from the lettuce plants (e.g., lettuce heads), and seeds produced therefrom where the lettuce plant is isolated by the breeding method of the invention.

BRIEF DESCRIPTION OF THE DRAWINGS

The patent or application file contains at least one drawing executed in color. Copies of this patent or patent application publication with color drawings will be provided by the office upon request and payment of the necessary fee.

FIG. 1A shows a head of lettuce variety 'Dark Horse'. FIG. 1B shows a bottom view of a head of lettuce variety 'Dark Horse'. FIG. 1C shows a bottom view of heads of lettuce variety 'Dark Horse'. FIG. 1D shows plants of lettuce variety 'Dark Horse'. FIG. 1E shows a top view of a head of lettuce variety 'Dark Horse'. FIG. 1F shows a bottom view of a head of lettuce variety 'Dark Horse'. FIG. 1G shows a cross-sectional view of a head of lettuce variety 'Dark Horse'.

FIG. 2A shows heads of lettuce varieties 'Showtime' (labeled PS1082, top) and 'Dark Horse' (bottom). FIG. 2W shows harvest-mature outer leaves of lettuce varieties 'Dark Horse' (top) and 'Greenbelt' (bottom).

FIG. 3A shows a bottom view of heads of lettuce variety 'Hotshot' (labeled 14RDSJV009-2). FIG. 3B shows a plant of lettuce variety 'Hotshot'. FIG. 3C shows seedlings of lettuce variety 'Hotshot'. FIG. 3D shows plants of lettuce variety 'Hotshot'. FIG. 3E shows a top view of a head of lettuce variety 'Hotshot'. FIG. 3F shows a bottom view of a head of lettuce variety 'Hotshot'. FIG. 3G shows a cross-sectional view of a head of lettuce variety 'Hotshot'. FIG. 3H shows a harvest-mature outer leaf of lettuce variety 'Hotshot'.

FIG. 4A shows plants of lettuce varieties 'Hotshot' (left) and 'El Guapo' (right). FIG. 4AA shows a harvest-mature outer leaf of lettuce variety 'Caretaker'.

FIG. 5A shows a bottom and cross-sectional view of heads of lettuce variety 'Uppercut' (14RDSJV013-1). FIG. 5B show plants of lettuce variety 'Uppercut'. FIG. 5C shows a top view of a head of lettuce variety 'Uppercut'. FIG. 5D shows a bottom view of a head of lettuce variety 'Uppercut'. FIG. 5E shows a cross-sectional view of a head of lettuce variety 'Uppercut'.

FIG. 6A show plants of lettuce variety 'Headmaster'. FIG. 6O shows a cross-sectional view of heads of lettuce varieties 'Thunderhead' (left) and 'Uppercut' (right). FIG. 6R shows harvest-mature outer leaves of lettuce varieties 'Headmaster' (top) and 'Uppercut' (bottom).

DETAILED DESCRIPTION

Definitions

Figure 1A:
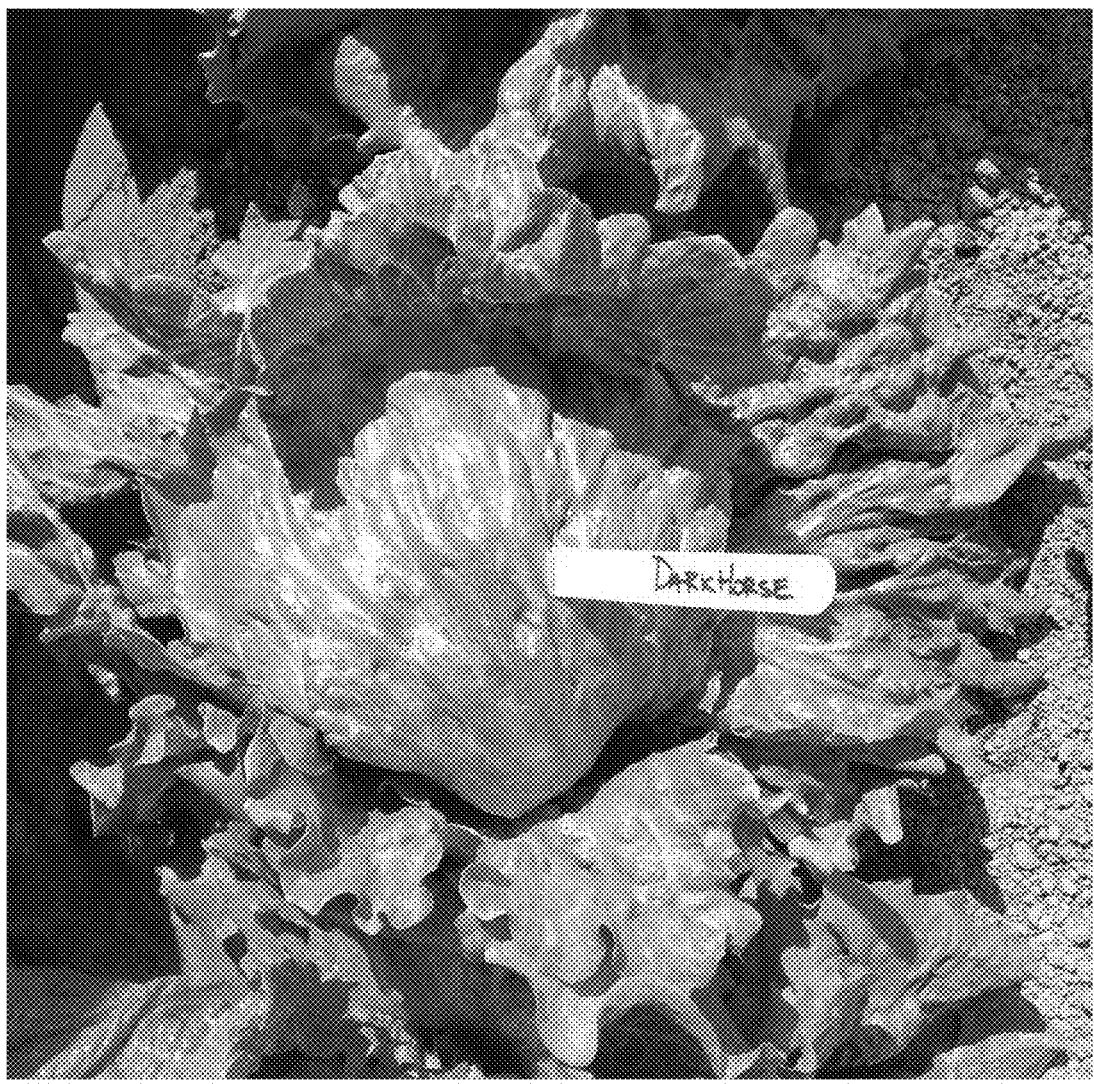
FIGS. 1A-1G show lettuce variety 'Dark Horse'.
Figure 1B:
Figure 1C:
Figure 1D:
Figure 1E:
Figure 1F:
Figure 1G:

In order to more clearly understand the invention, the following definitions are provided:

Core Diameter: Core diameter is the diameter of the lettuce stem at the base of the cut head.

Core Length: Core length is the length of the vertically sliced lettuce plant as measured from the base of the cut stem to the top of the apex (growing point).

*Fusarium* Wilt: *Fusarium* wilt of lettuce is a disease caused by the fungus *Fusarium oxysporum* f. sp. *lactucae* that causes infected seedlings to wilt, and turn red or brown in color in inner tissues, and causes leaves of infected older plants to turn yellow and develop tip burn.

Head Diameter: Head diameter is the diameter of the vertically sliced lettuce plant head at its widest horizontal point, perpendicular to the stem.

Head Length: Head length is the diameter of the vertically sliced lettuce plant head as measured from the base of the cut stem to the cap leaf.

Head Weight: Head weight is the weight of the marketable lettuce plant, cut and trimmed to market specifications.

Heart Length: Heart length is the length of the vertically sliced lettuce plant as measured from the base of the cut stem to the top leaf margin of the longest outermost leaf that encloses the green leaf heart.

Lettuce Mosaic Virus: A disease that can cause a stunted, deformed, or mottled pattern in young lettuce and yellow, twisted, and deformed leaves in older lettuce.

Maturity Date: Maturity refers to the stage when the plants are of full size or optimum weight, in marketable form or shape to be of commercial or economic value.

Munsell: Munsell refers to the Munsell Color Chart, which uses the Munsell color system.

*Nasonovia ribisnigri*: A leaf aphid that colonizes the innermost leaves of the lettuce plant, contaminating areas that cannot be treated easily with insecticides.

Plant Diameter: The plant diameter is a measurement across the top of the lettuce plant at its widest point. The measurement of frame diameter is taken from the outer most leaf tip horizontally to the outer most leaf tip.

Tip burn: Means a browning of the edges or tips of lettuce leaves that is a physiological response to a lack of calcium.

Taking into account these definitions, the present invention is directed to seeds of the lettuce varieties 'Dark Horse', 'Hotshot', and 'Uppercut', plants produced by growing 'Dark Horse', 'Hotshot', and/or 'Uppercut' lettuce seeds, heads isolated or harvested from the plants, one or more plants selected from a collection of 'Dark Horse', 'Hotshot', and/or 'Uppercut' plants and seeds derived or produced therefrom; plants produced by crossing a lettuce plant with a 'Dark Horse', 'Hotshot', and/or 'Uppercut' lettuce plant and seeds derived or produced therefrom.

Objective Description of the Variety 'Dark Horse'

'Dark Horse' is an open-pollinated iceberg lettuce variety. This variety is distinct and unique to all other iceberg lettuce varieties due to its larger frame and larger head diameter. Moreover, 'Dark Horse' has a growing season that includes autumn and winter, is suitable for cultivation in the open, and is adapted to growing in regions in the Southwest, such the Arizona desert, as well as the West Coast regions of the United States. FIGS. 1A-1G depict heads and plants of lettuce variety 'Dark Horse'. Lettuce variety 'Dark Horse' is the result of numerous generations of plant selections chosen for its increased weight.

The variety has shown uniformity and stability for the traits, within the limits of environmental influence for the traits. It has been self-pollinated a sufficient number of generations with careful attention to uniformity of plant type. The line has been increased with continued observation for uniformity. No variant traits have been observed or are expected in variety 'Dark Horse'.

Lettuce variety 'Dark Horse' has the following morphologic and other characteristics:

Plant type: Crisp (i.e., iceberg)
Seed:
Color: Munsell 5YR 3/2 (Black)
Light dormancy: Light not required
Heat dormancy: Susceptible
Cotyledon to Fourth Leaf Stage:
Shape of cotyledons: Broad
Shape of fourth leaf: Oval
Apical margin: Crenate/gnawed
Basal margin: Coarsely dentate
Green color: Medium green
Anthocyanin distribution: Absent
Cupping: Slight
Reflexing: None
Mature Leaves:
Margin:
Incision depth: Moderate
Indentation: Crenate
Undulation of apical margin: Strong
Green color: Munsell 5GY 5/6 (Medium green)
Anthocyanin distribution: Absent
Leaf glossiness: Dull
Blistering: Moderate
Leaf thickness: Intermediate
Trichomes: Absent (smooth)

Plant:
Spread of frame leaves: 48.5 cm
Head diameter (market trimmed with single cap leaf): 16.2 cm
Head shape: Spherical
Head size class: Large
Head firmness: Firm
Butt:
Butt shape: Rounded
Midrib: Moderately raised
Core:
Core diameter at base of head: 31.6 mm
Ratio of head diameter/core diameter: 5.1
Core height from base of head to apex: 38.6 mm
Bolting:
Number of days from first water to seed stalk emergence under summer conditions: 72 days
Bolting class: Medium
Mature seed stalk height: 117 cm
Mature seed stalk spread: 42.8 cm
Spread of bolter plant at widest point: 32.3 cm
Bolter leaves: Curved
Margin: Dentate
Bolter habit:
Terminal inflorescence: Present
Lateral shoots: Present
Basal side shoots: Absent
Disease Resistance:
Downy Mildew (*Bremia lactucae*) (Bl): Susceptible to Bl:16-18, Bl:20-27, Bl:29-Bl:31, and Bl:33
Lettuce mosaic virus (LMV) strain Ls-1: Susceptible
Big Vein Virus: Susceptible
Powdery Mildew: Susceptible
Pest Resistance:
*Nasonovia ribisnigri* biotype 0 (Nr:0): Susceptible
Stress Resistance:
Heat: Moderately resistant/moderately susceptible
Cold: Moderately resistant/moderately susceptible
Comparisons to Other Lettuce Variety Table 1A below compares characteristics of lettuce variety 'Dark Horse' with the lettuce variety 'Showtime' (PVP Certificate No. 200700432). Column 1 lists the characteristics, column 2 shows the characteristics for lettuce variety 'Dark Horse', and column 3 shows the characteristics for lettuce variety 'Showtime'.

TABLE 1A

| Characteristic | 'Dark Horse' | 'Showtime' |
|---|---|---|
| Frame size | Larger frame | Smaller frame |
| Weight | Increased weight | Decreased weight |
| Head diameter | Increased head diameter | Decreased head diameter |

Table 1B below compares characteristics of lettuce variety 'Dark Horse' with the lettuce variety 'Showtime'. Column 1 lists the characteristics, column 2 shows the characteristics for lettuce variety 'Dark Horse', and column 3 shows the characteristics for lettuce variety 'Showtime'.

TABLE 1B

| Characteristic | 'Dark Horse' | 'Showtime' |
|---|---|---|
| Mature seed stalk height | 117 cm | 103.4 cm |
| Mature seed stalk spread | 42.8 cm | 54.8 cm |
| Spread of bolter plant at widest point | 32.3 cm | 33.5 cm |

Table 1C below compares characteristics of lettuce variety 'Dark Horse' with the lettuce varieties 'Showtime' and 'Greenbelt'. Column 1 lists the characteristics, column 2 shows the characteristics for lettuce variety 'Dark Horse', column 3 shows the characteristics for lettuce variety 'Showtime', and column 4 shows the characteristics for lettuce variety 'Greenbelt'.

TABLE 1C

| Characteristic | 'Dark Horse' | 'Showtime' | 'Greenbelt' |
|---|---|---|---|
| Spread of frame leaves | 48.5 cm | 44.5 cm | 45.3 cm |
| Head weight | 751.5 g | 639.1 g | 643.3 g |
| Head diameter (market trimmed with single cap leaf) | 161.5 mm | 132.7 mm | 140.2 mm |
| Core diameter at base of head | 31.6 mm | 31.9 mm | 32.3 mm |
| Core height from base of head to apex | 38.6 mm | 32.1 mm | 31.4 mm |
| Ratio of head diameter/core diameter | 5.1 | 4.2 | 4.34 |
| Color of mature outer leaves (Munsell) | 5GY 5/6 | 5GY 5/6 | 5GY 5/10 |

Tables 2A and 2B below show results of a trial that compares the head weight, head diameter, core length, core diameter, and frame diameter of 20 plants of the lettuce variety 'Dark Horse' (Table 2A) with those of 20 plants of lettuce variety 'Showtime' (Table 2B).

TABLE 2A

| 'Dark Horse' | Head Wt. | Head Diameter | Core Length | Core Diameter | Frame Diameter |
|---|---|---|---|---|---|
| Max | 635 g | 182 mm | 43 mm | 34 mm | 61.5 cm |
| Min | 500 g | 139 mm | 21 mm | 28 mm | 45.5 cm |
| Average | 555 g | 161.05 mm | 31.85 mm | 30.55 mm | 56.58 cm |
| Std. Dev | 36.99 | 13.79 | 5.25 | 1.61 | 4.06 |

TABLE 2B

| 'Showtime' | Head Wt. | Head Diameter | Core Length | Core Diameter | Frame Diameter |
|---|---|---|---|---|---|
| Max | 450 g | 151 mm | 28 mm | 30 mm | 51.5 cm |
| Min | 350 g | 132 mm | 14 mm | 25 mm | 42.5 cm |
| Average | 406 g | 141.1 mm | 20.95 mm | 27.4 mm | 46.83 cm |
| Std. Dev | 26.88 | 6.26 | 3.69 | 1.57 | 2.83 |

Tables 2C-2E below show results of a first trial that compares the head weight, head diameter, core length, core diameter, and frame diameter of 20 plants of the lettuce variety 'Dark Horse' (Table 2C) with those of 20 plants of lettuce variety 'Showtime' (Table 2D) and 20 plants of lettuce variety 'Greenbelt' (Table 2E).

TABLE 2C

| 'Dark Horse' | Head Wt. | Head Diameter | Core Length | Core Diameter | Frame Diameter |
|---|---|---|---|---|---|
| Max | 1450 g | 170 mm | 73 mm | 40 mm | 55 cm |
| Min | 410 g | 119 mm | 29 mm | 26 mm | 38 cm |
| Average | 950 g | 143.15 mm | 50.25 mm | 32.35 mm | 47.3 cm |
| Std. Dev | 254.71 | 13.26 | 13.93 | 3.80 | 4.96 |

TABLE 2D

| 'Showtime' | Head Wt. | Head Diameter | Core Length | Core Diameter | Frame Diameter |
|---|---|---|---|---|---|
| Max | 1170 g | 142 mm | 55 mm | 41 mm | 47 cm |
| Min | 595 g | 104 mm | 21 mm | 27 mm | 37 cm |
| Average | 802.5 g | 117.25 mm | 32.25 mm | 33.2 mm | 42.4 cm |
| Std. Dev | 150.01 | 10.23 | 8.19 | 3.17 | 3.14 |

TABLE 2E

| 'Greenbelt' | Head Wt. | Head Diameter | Core Length | Core Diameter | Frame Diameter |
|---|---|---|---|---|---|
| Max | 1040 g | 140 mm | 60 mm | 40 mm | 51 cm |
| Min | 555 g | 110 mm | 20 mm | 28 mm | 37 cm |
| Average | 810.75 g | 125.1 mm | 41.55 mm | 34.05 mm | 44.5 cm |
| Std. Dev | 125.52 | 10.49 | 10.26 | 4.08 | 4.73 |

Tables 2F-2H below show results of a second trial that compares the head weight, head diameter, core length, core diameter, and frame diameter of 20 plants of the lettuce variety 'Dark Horse' (Table 2F) with those of 20 plants of lettuce variety 'Showtime' (Table 2G) and 20 plants of lettuce variety 'Greenbelt' (Table 2H).

TABLE 2F

| 'Dark Horse' | Head Wt. | Head Diameter | Core Length | Core Diameter | Frame Diameter |
|---|---|---|---|---|---|
| Max | 700 g | 195 mm | 34 mm | 34 mm | 53 cm |
| Min | 385 g | 166 mm | 21 mm | 25 mm | 46 cm |
| Average | 553 g | 179.8 mm | 27 mm | 30.75 mm | 49.7 cm |
| Std. Dev | 97.54 | 7.43 | 3.18 | 2.07 | 1.75 |

TABLE 2G

| 'Showtime' | Head Wt. | Head Diameter | Core Length | Core Diameter | Frame Diameter |
|---|---|---|---|---|---|
| Max | 620 g | 158 mm | 43 mm | 34 mm | 50 cm |
| Min | 390 g | 138 mm | 21 mm | 28 mm | 42 cm |
| Average | 475.75 g | 148.1 mm | 31.85 mm | 30.55 mm | 46.5 cm |
| Std. Dev | 71.90 | 6.41 | 5.25 | 1.61 | 2.24 |

TABLE 2H

| 'Greenbelt' | Head Wt. | Head Diameter | Core Length | Core Diameter | Frame Diameter |
|---|---|---|---|---|---|
| Max | 615 g | 167 mm | 28 mm | 34 mm | 50 cm |
| Min | 355 g | 143 mm | 15 mm | 28 mm | 43 cm |
| Average | 475.75 g | 155.3 mm | 21.3 mm | 30.55 mm | 46.5 cm |
| Std. Dev | 77.09 | 6.91 | 3.50 | 1.85 | 1.82 |

Figure 2A:
FIGS. 2A-2W show comparisons between lettuce varieties 'Dark Horse', 'Showtime', and 'Greenbelt'.
Figure 2B:
FIG. 2B shows a bottom view of heads of lettuce varieties 'Showtime' (labeled PS1082, top) and 'Dark Horse' (bottom).
Figure 2C:
FIG. 2C shows a cross-sectional view of heads of lettuce varieties 'Showtime' (labeled PS1082, top) and 'Dark Horse' (bottom).
Figure 2D:
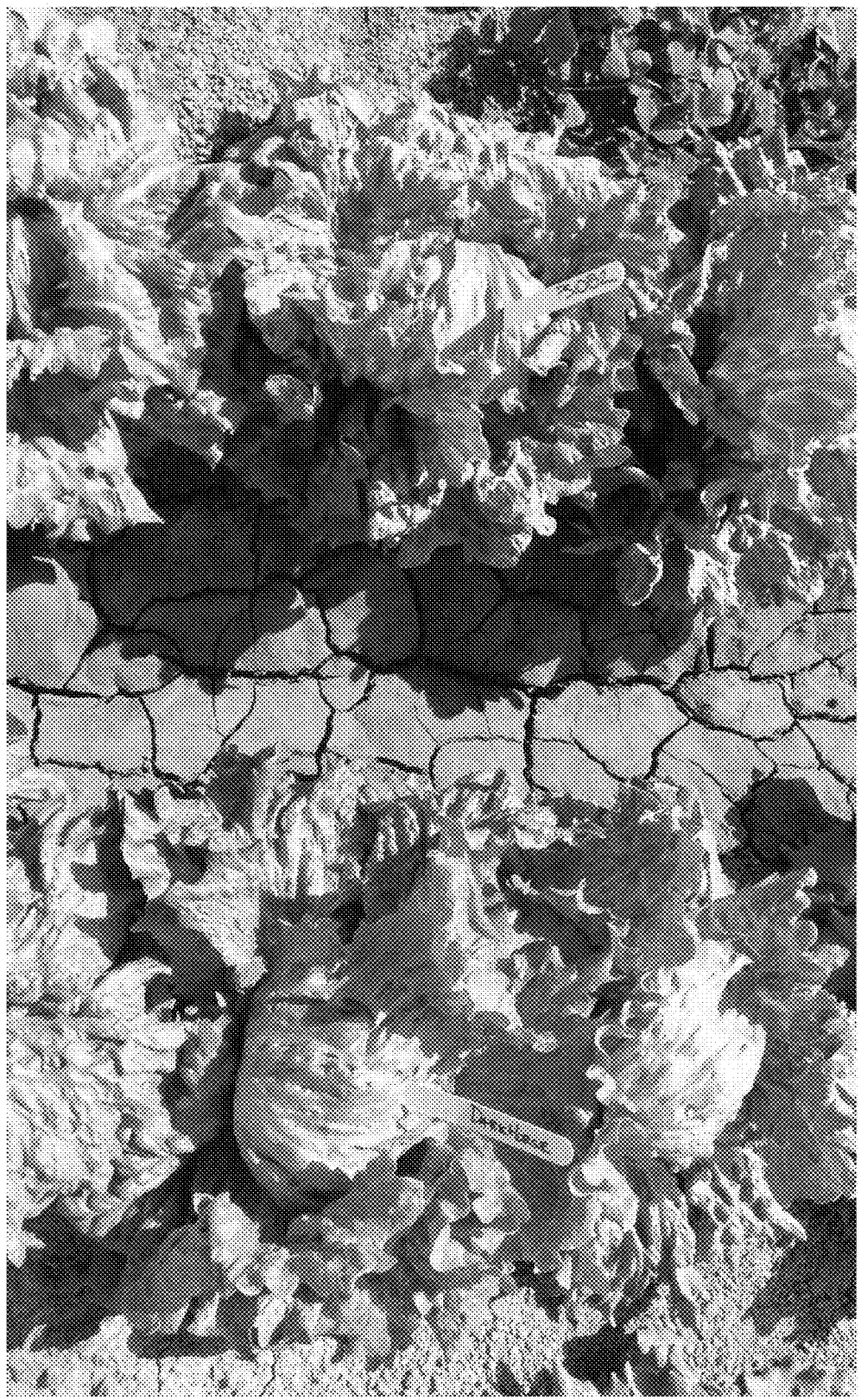
FIG. 2D shows plants of lettuce varieties 'Showtime' (labeled PS1082, top) and 'Dark Horse' (bottom).
Figure 2E:
FIG. 2E shows a bottom view of heads of lettuce variety 'Showtime' (labeled PS1082).
Figure 2F:
FIG. 2F shows a head of lettuce variety 'Showtime' (labeled PS1082).
Figure 2G:
FIG. 2G shows a bottom view of a head of lettuce variety 'Showtime' (labeled PS1082).
Figure 2H:
FIG. 2H shows plants of lettuce variety 'Showtime'.
Figure 2I:
FIG. 2I shows plants of lettuce variety 'Greenbelt'.
Figure 2J:
FIG. 2J shows a top view of a head of lettuce variety 'Showtime'.
Figure 2K:
FIG. 2K shows a bottom view of a head of lettuce variety 'Showtime'.
Figure 2L:
FIG. 2L shows a cross-sectional view of a head of lettuce variety 'Showtime'.
Figure 2M:
FIG. 2M shows a top view of a head of lettuce variety 'Greenbelt'.
Figure 2N:
FIG. 2N shows a bottom view of a head of lettuce variety 'Greenbelt'.
Figure 2O:
FIG. 2O shows a cross-sectional view of a head of lettuce variety 'Greenbelt'.
Figure 2P:
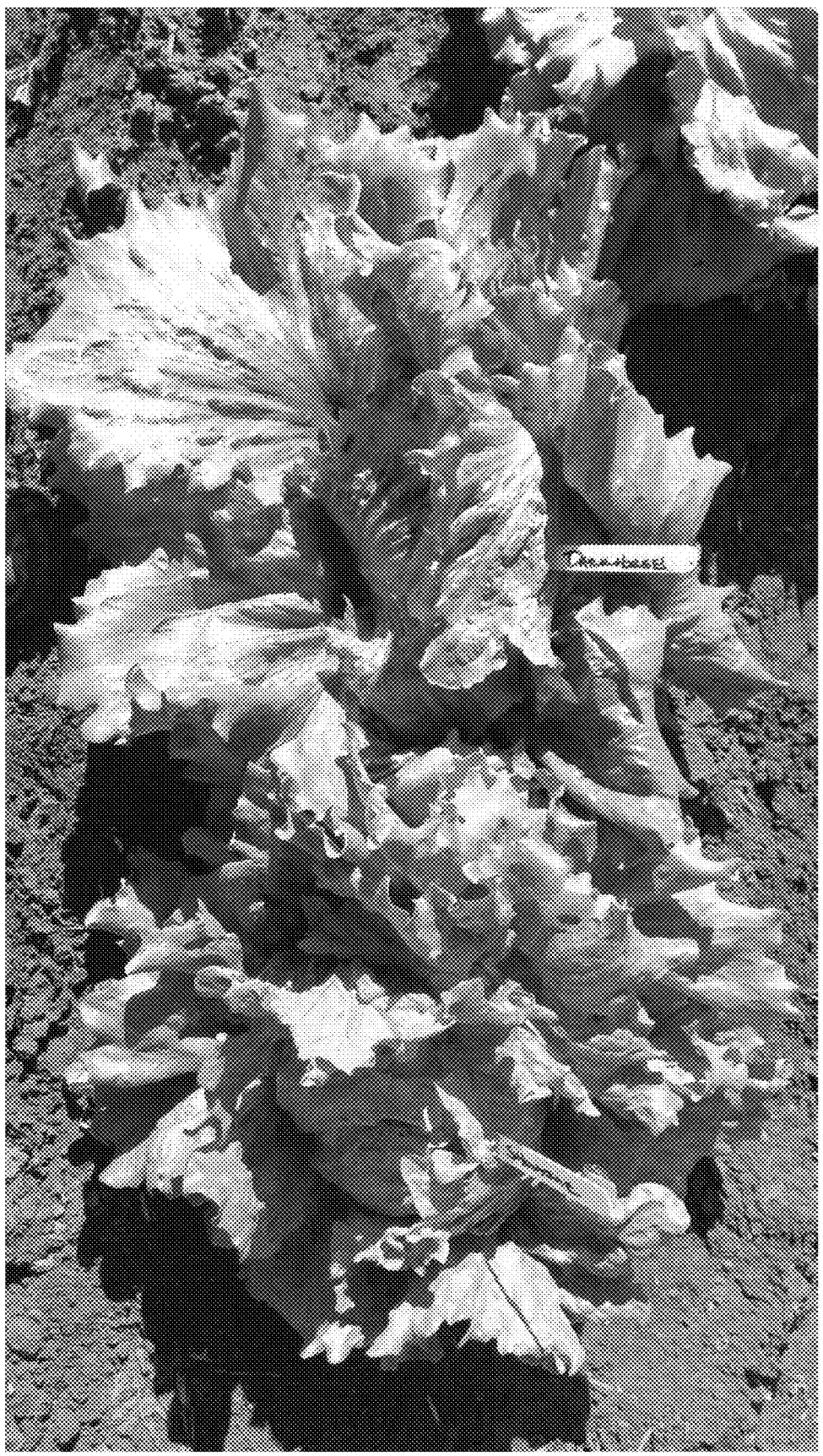
FIG. 2P shows a top view of heads of lettuce varieties 'Dark Horse' (top) and 'Showtime' (bottom).
Figure 2Q:
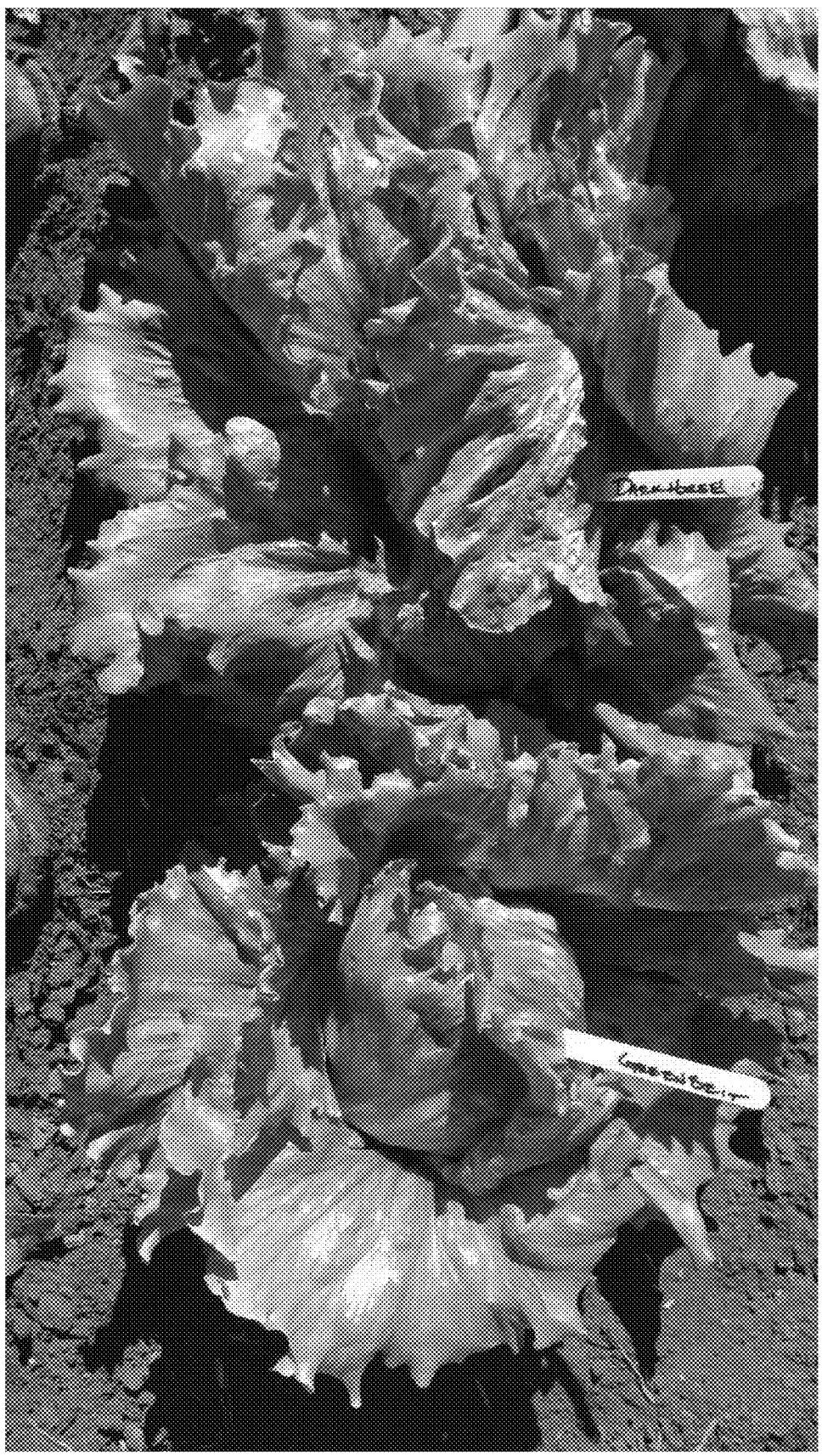
FIG. 2Q shows a top view of heads of lettuce varieties 'Dark Horse' (top) and 'Greenbelt' (bottom).
Figure 2R:
FIG. 2R shows a bottom view of heads of lettuce varieties 'Dark Horse' (top) and 'Showtime' (bottom).
Figure 2S:
FIG. 2S shows a bottom view of heads of lettuce varieties 'Dark Horse' (top) and 'Greenbelt' (bottom).
Figure 2T:
FIG. 2T shows a cross-sectional view of heads of lettuce varieties 'Dark Horse' (top) and 'Showtime' (bottom).
Figure 2U:
FIG. 2U shows a cross-sectional view of heads of lettuce varieties 'Dark Horse' (top) and 'Greenbelt' (bottom).
Figure 2V:
FIG. 2V shows harvest-mature outer leaves of lettuce varieties 'Dark Horse' (top) and 'Showtime' (bottom).
Figure 2W:
Figure 3A:
FIGS. 3A-3H show lettuce variety 'Hotshot'.
Figure 3B:
Figure 3C:
Figure 3D:
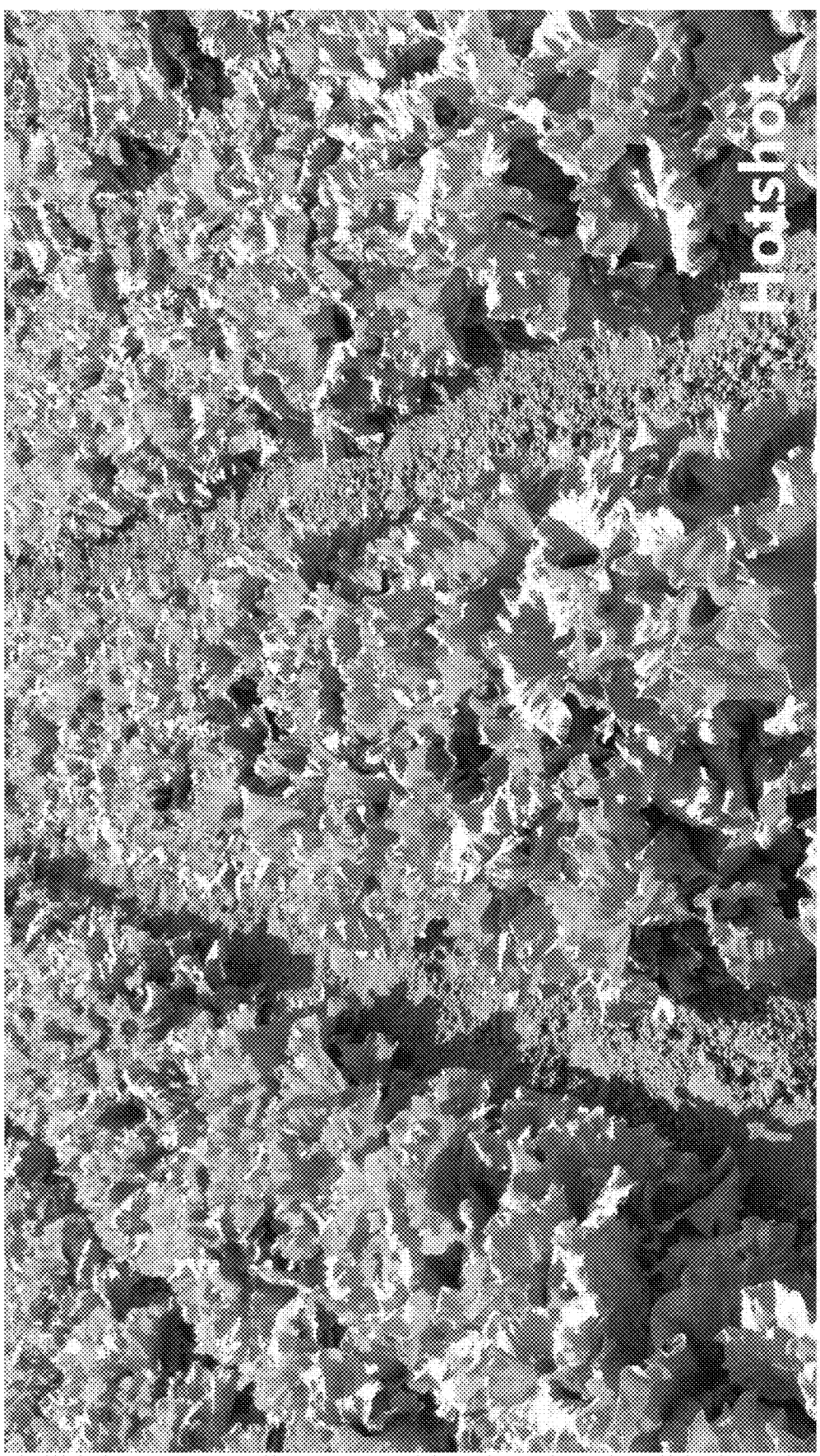
Figure 3E:
Figure 3F:
Figure 3G:
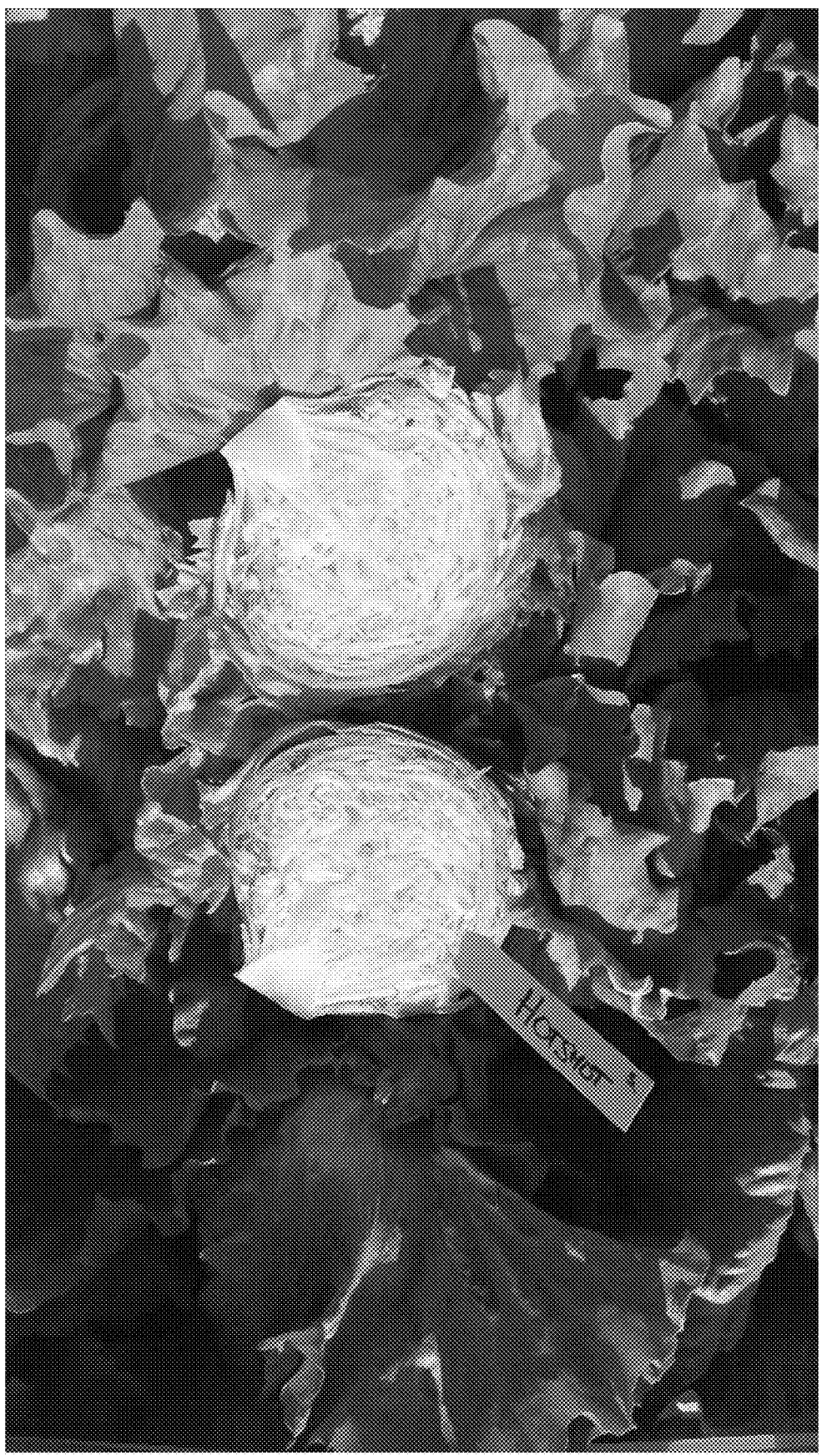
Figure 3H:

Further distinguishing features are apparent from the comparison of the varieties 'Dark Horse', 'Showtime', and 'Greenbelt' depicted in FIGS. 2A-2W.

Objective Description of the Variety 'Hotshot'

'Hotshot' is an open-pollinated iceberg lettuce variety. This variety is distinct and unique to all other iceberg lettuce varieties due to its earlier maturing time, smaller stem length, darker green color, crisp leaf texture, larger head diameter, larger core diameter, and increased weight. Moreover, 'Hotshot' has a growing season that includes autumn, is suitable for cultivation in the open, and is adapted to growing in regions in the Southwest, such the Arizona desert, of the United States. FIGS. 3A-3H depict heads, plants, seedlings, and a harvest-mature outer leaf of lettuce variety 'Hotshot'. Lettuce variety 'Hotshot' is the result of numerous generations of plant selections chosen for its intermediate resistance to *Fusarium* Wilt race 1.

The variety has shown uniformity and stability for the traits, within the limits of environmental influence for the traits. It has been self-pollinated a sufficient number of generations with careful attention to uniformity of plant type. The line has been increased with continued observation for uniformity. No variant traits have been observed or are expected in variety 'Hotshot'.

Lettuce variety 'Hotshot' has the following morphologic and other characteristics:
Plant type: Crisp (i.e., iceberg)
Seed:
Color: Munsell 2.5Y7/2 (White)
Seed light dormancy: Light not required
Heat dormancy: Susceptible
Cotyledon to Fourth Leaf Stage:
Shape of cotyledons: Intermediate
Shape of fourth leaf: Elongated
Apical margin: Entire
Basal margin: Finely dentate
Green color: Medium green
Anthocyanin distribution: Absent
Cupping: Slight
Reflexing: None
Mature Leaves:
Margin:
Incision depth: Moderate
Indentation: Deeply dentate
Undulation of apical margin: Strong
Green color: Munsell 5GY 5/6 (Medium green)
Anthocyanin distribution: Absent
Leaf glossiness: Glossy
Blistering: Moderate
Leaf thickness: Intermediate
Trichomes: Absent (smooth)
Texture: Crisp
Plant:
Spread of frame leaves: 50.8 cm
Head diameter (market trimmed with single cap leaf): 14.4 cm
Head shape: Spherical
Head size class: Medium
Head firmness: Firm
Butt:
Butt shape: Rounded
Midrib: Moderately raised
Core:
Core diameter at base of head: 30.1 mm
Ratio of head diameter/core diameter: 4.8
Core height from base of head to apex: 26.8 mm
Bolting:
Number of days from first water to seed stalk emergence under summer conditions: 74
Bolting class: Medium
Mature seed stalk height: 107 cm
Mature seed stalk spread: 50.9 cm
Spread of bolter plant at widest point: 37.4 cm
Bolter leaves: Curved
Margin: Dentate
Bolter habit:
Terminal inflorescence: Absent
Lateral shoots: Present
Basal side shoots: Absent
Disease Resistance:
Big Vein Virus: Susceptible
Downy Mildew (*Bremia lactucae*) (Bl): Susceptible to Bl:16-18, Bl:20-27, Bl:29-Bl:31, and Bl:33
Lettuce mosaic virus (LMV) strain Ls-1: Susceptible
*Fusarium* Wilt (*Fusarium oxysporum* f. sp. *lactucae*) race 1: Intermediate resistant
Pests:
*Nasonovia ribisnigri* biotype 0 (Nr:0): Susceptible
Stress Resistance:
Tipburn: Susceptible
Heat: Moderately resistant/moderately susceptible
Cold: Susceptible
Pink rib: Moderately resistant/moderately susceptible Comparisons to Other Lettuce Variety Table 3A below compares characteristics of lettuce variety 'Hotshot' with the lettuce variety 'Caretaker' (PVP Certificate No. 201000303). Column 1 lists the characteristics, column 2 shows the characteristics for lettuce variety 'Hotshot', and column 3 shows the characteristics for lettuce variety 'Caretaker'. Texture refers to resilient and crisp leaf thickness at the proper maturity of harvest.

TABLE 3A

| Characteristic | 'Hotshot' | 'Caretaker' |
|---|---|---|
| Maturing time | Earlier maturing | Later maturing |
| Stem length | Shorter stem length | Longer stem length |
| Green color | Darker green color | Lighter green color |
| Texture | More textured | Less textured |

Table 3B below compares characteristics of lettuce variety 'Hotshot' with the lettuce variety 'Caretaker' (PVP Certificate No. 201000303) and lettuce variety 'Raider' (PVP Certificate No. PVP 8900281). Column 1 lists the characteristics, column 2 shows the characteristics for lettuce variety 'Hotshot', column 3 shows the characteristics for lettuce variety 'Caretaker', and column 4 shows the characteristics for lettuce variety 'Raider'.

TABLE 3B

| Characteristic | 'Hotshot' | 'Caretaker' | 'Raider' |
|---|---|---|---|
| Spread of frame leaves | 50.8 cm | 50.3 cm | 51.9 cm |
| Head weight | 611.7 g | 551 g | 570.3 g |
| Head diameter (market trimmed with single cap leaf) | 144.1 mm | 138.4 mm | 140.5 mm |
| Core diameter at base of head | 30.1 mm | 29.5 mm | 29.6 mm |
| Core height from base of head to apex | 26.8 mm | 27.8 mm | 29.6 mm |

TABLE 3B-continued

| Characteristic | 'Hotshot' | 'Caretaker' | 'Raider' |
|---|---|---|---|
| Ratio of head diameter/core diameter | 4.8 | 4.7 | 4.8 |
| Color of mature outer leaves (Munsell) | 5GY 5/6 | 5GY 5/8 | 5GY 5/10 |

Tables 4A-4C below show results of a first trial that compares the head weight, head diameter, core length, core diameter, and frame diameter of 20 plants of the lettuce variety 'Hotshot' (Table 4A) with those of 20 plants of lettuce variety 'Caretaker' (Table 4B) and 20 plants of variety 'Raider' (Table 4C).

TABLE 4A

| 'Hotshot' | Head Wt. | Head Diameter | Core Length | Core Diameter | Frame Diameter |
|---|---|---|---|---|---|
| Max | 710 g | 163 mm | 40 mm | 39 mm | 54 cm |
| Min | 480 g | 124 mm | 28 mm | 32 mm | 46 cm |
| Average | 609.25 g | 144.9 mm | 33.5 mm | 35.85 mm | 50.4 cm |
| Std. Dev | 66.89 | 10.15 | 3.22 | 2.03 | 2.35 |

TABLE 4B

| 'Caretaker' | Head Wt. | Head Diameter | Core Length | Core Diameter | Frame Diameter |
|---|---|---|---|---|---|
| Max | 640 g | 151 mm | 39 mm | 39 mm | 54 cm |
| Min | 420 g | 124 mm | 25 mm | 32 mm | 46 cm |
| Average | 521.5 g | 138.9 mm | 31.85 mm | 34.35 mm | 49.55 cm |
| Std. Dev | 67.44 | 7.82 | 3.62 | 1.53 | 2.42 |

TABLE 4C

| 'Raider' | Head Wt. | Head Diameter | Core Length | Core Diameter | Frame Diameter |
|---|---|---|---|---|---|
| Max | 615 g | 152 mm | 40 mm | 39 mm | 57 cm |
| Min | 370 g | 124 mm | 29 mm | 32 mm | 48 cm |
| Average | 486 g | 138.35 mm | 34.5 mm | 35.2 mm | 52.3 cm |
| Std. Dev | 68.20 | 7.05 | 3.38 | 2.00 | 2.27 |

Tables 4D-4F below show results of a second trial that compares the head weight, head diameter, core length, core diameter, and frame diameter of 20 plants of the lettuce variety 'Hotshot' (Table 4D) with those of 20 plants of lettuce variety 'Caretaker' (Table 4E) and 20 plants of variety 'Raider' (Table 4F).

TABLE 4D

| 'Hotshot' | Head Wt. | Head Diameter | Core Length | Core Diameter | Frame Diameter |
|---|---|---|---|---|---|
| Max | 815 g | 149 mm | 34 mm | 37 mm | 59 cm |
| Min | 550 g | 125 mm | 22 mm | 28 mm | 51 cm |
| Average | 659.25 g | 137.9 mm | 28.9 mm | 32.55 mm | 54.65 cm |
| Std. Dev | 67.34 | 7.38 | 3.37 | 2.24 | 2.46 |

TABLE 4E

| 'Caretaker' | Head Wt. | Head Diameter | Core Length | Core Diameter | Frame Diameter |
|---|---|---|---|---|---|
| Max | 710 g | 149 mm | 33 mm | 34 mm | 59 cm |
| Min | 425 g | 117 mm | 24 mm | 27 mm | 51 cm |
| Average | 567.25 g | 130.95 mm | 28.45 mm | 31.35 mm | 54.05 cm |
| Std. Dev | 81.10 | 8.33 | 2.96 | 1.98 | 2.26 |

TABLE 4F

| 'Raider' | Head Wt. | Head Diameter | Core Length | Core Diameter | Frame Diameter |
|---|---|---|---|---|---|
| Max | 930 g | 151 mm | 38 mm | 37 mm | 61 cm |
| Min | 485 g | 116 mm | 24 mm | 29 mm | 52 cm |
| Average | 630.75 g | 134.1 mm | 30.35 mm | 33.45 mm | 57.1 cm |
| Std. Dev | 115.84 | 9.27 | 3.69 | 2.21 | 2.49 |

Tables 4G-4I below show results of a third trial that compares the head weight, head diameter, core length, core diameter, and frame diameter of 20 plants of the lettuce variety 'Hotshot' (Table 4G) with those of 20 plants of lettuce variety 'Caretaker' (Table 4H) and 20 plants of variety 'Raider' (Table 4I).

TABLE 4G

| 'Hotshot' | Head Wt. | Head Diameter | Core Length | Core Diameter | Frame Diameter |
|---|---|---|---|---|---|
| Max | 680 g | 175 mm | 21 mm | 25 mm | 50 cm |
| Min | 460 g | 132 mm | 15 mm | 20 mm | 44 cm |
| Average | 566.5 g | 149.6 mm | 17.9 mm | 21.95 mm | 47.45 cm |
| Std. Dev | 55.13 | 11.97 | 1.52 | 1.39 | 1.57 |

TABLE 4H

| 'Caretaker' | Head Wt. | Head Diameter | Core Length | Core Diameter | Frame Diameter |
|---|---|---|---|---|---|
| Max | 640 g | 156 mm | 26 mm | 25 mm | 51 cm |
| Min | 490 g | 132 mm | 19 mm | 21 mm | 43 cm |
| Average | 564.25 g | 145.3 mm | 23 mm | 22.9 mm | 47.45 cm |
| Std. Dev | 43.93 | 8.49 | 1.97 | 0.91 | 1.93 |

TABLE 4I

| 'Raider' | Head Wt. | Head Diameter | Core Length | Core Diameter | Frame Diameter |
|---|---|---|---|---|---|
| Max | 680 g | 176 mm | 26 mm | 23 mm | 50 cm |
| Min | 470 g | 130 mm | 20 mm | 16 mm | 43 cm |
| Average | 594 g | 149.05 mm | 24 mm | 20 mm | 46.35 cm |
| Std. Dev | 63.07 | 11.20 | 1.72 | 2.08 | 2.01 |

Figure 4A:
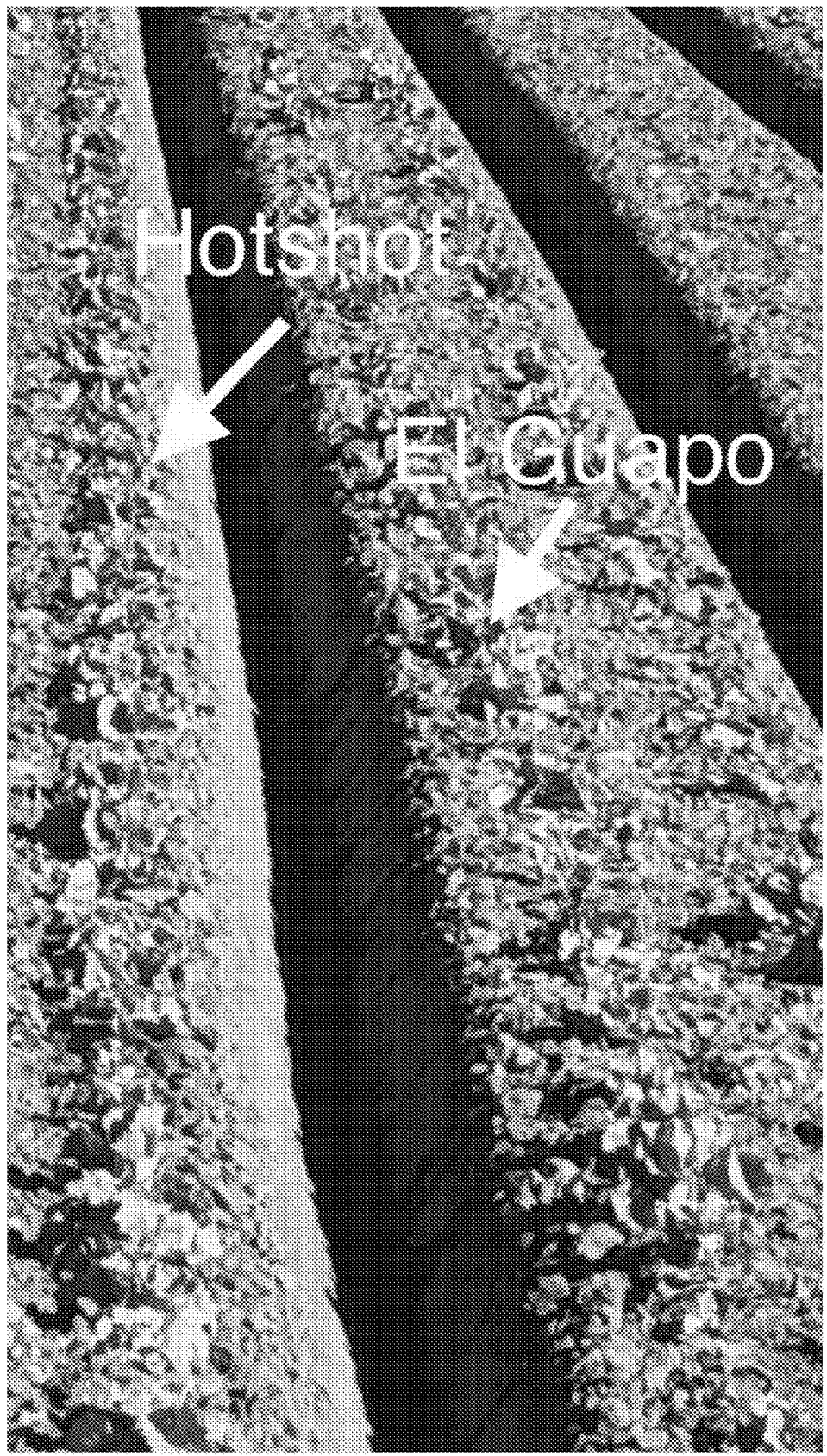
FIGS. 4A-4AA show comparisons between lettuce varieties 'Hotshot', 'El Guapo', 'Caretaker' (labeled PS1080), and 'Raider'.
Figure 4B:
FIG. 4B shows a bottom view of heads of lettuce of variety 'Caretaker' (labeled PS1080).
Figure 4C:
FIG. 4C shows a cross-sectional view of heads of lettuce of varieties 'Hotshot' (labeled 14RDSJV009-2, bottom) and 'Caretaker' (labeled PS1080, top).
Figure 4D:
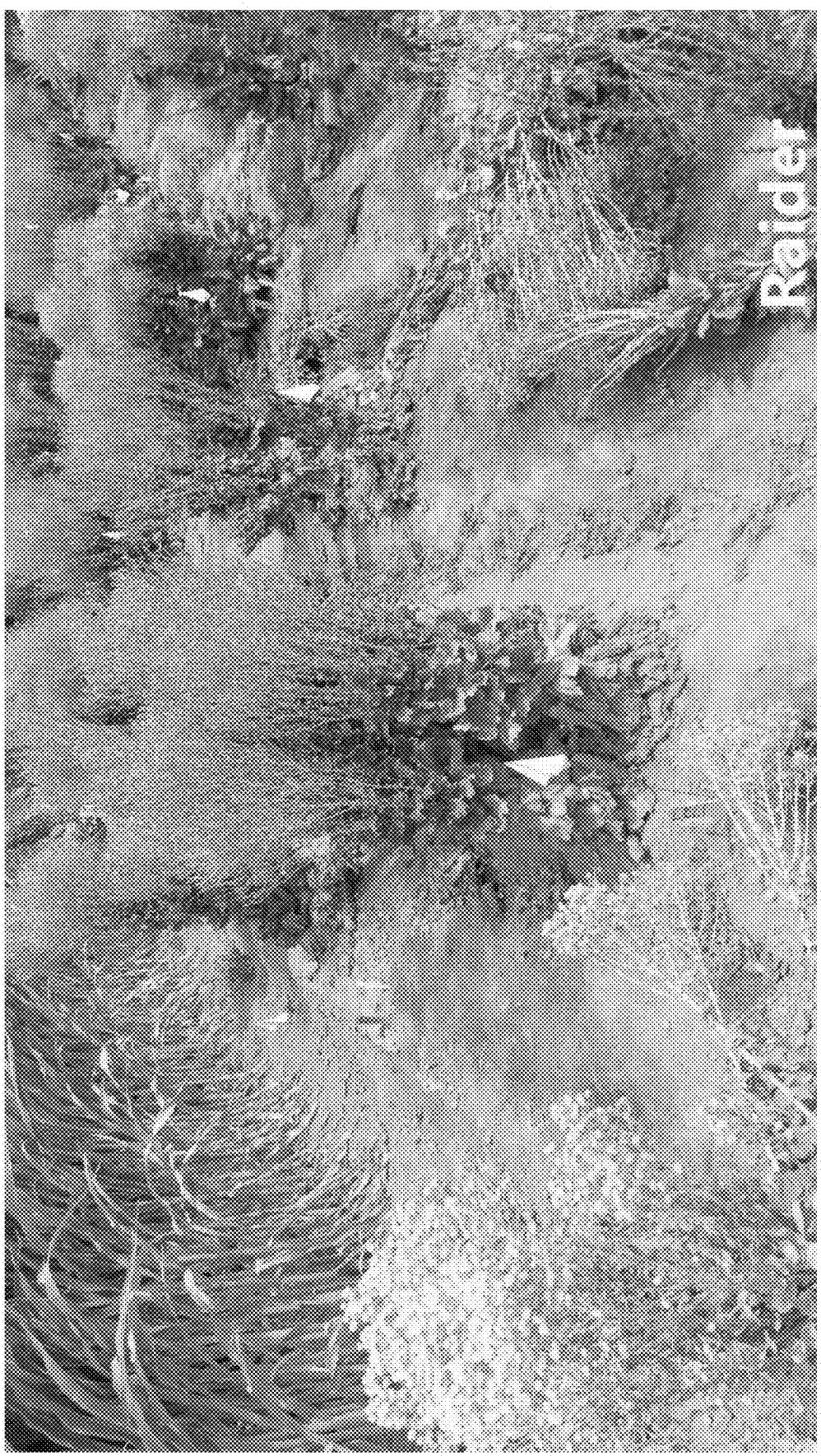
FIG. 4D shows plants of lettuce variety 'Raider'.
Figure 4E:
FIG. 4E shows plants of lettuce variety 'Caretaker'.
Figure 4F:
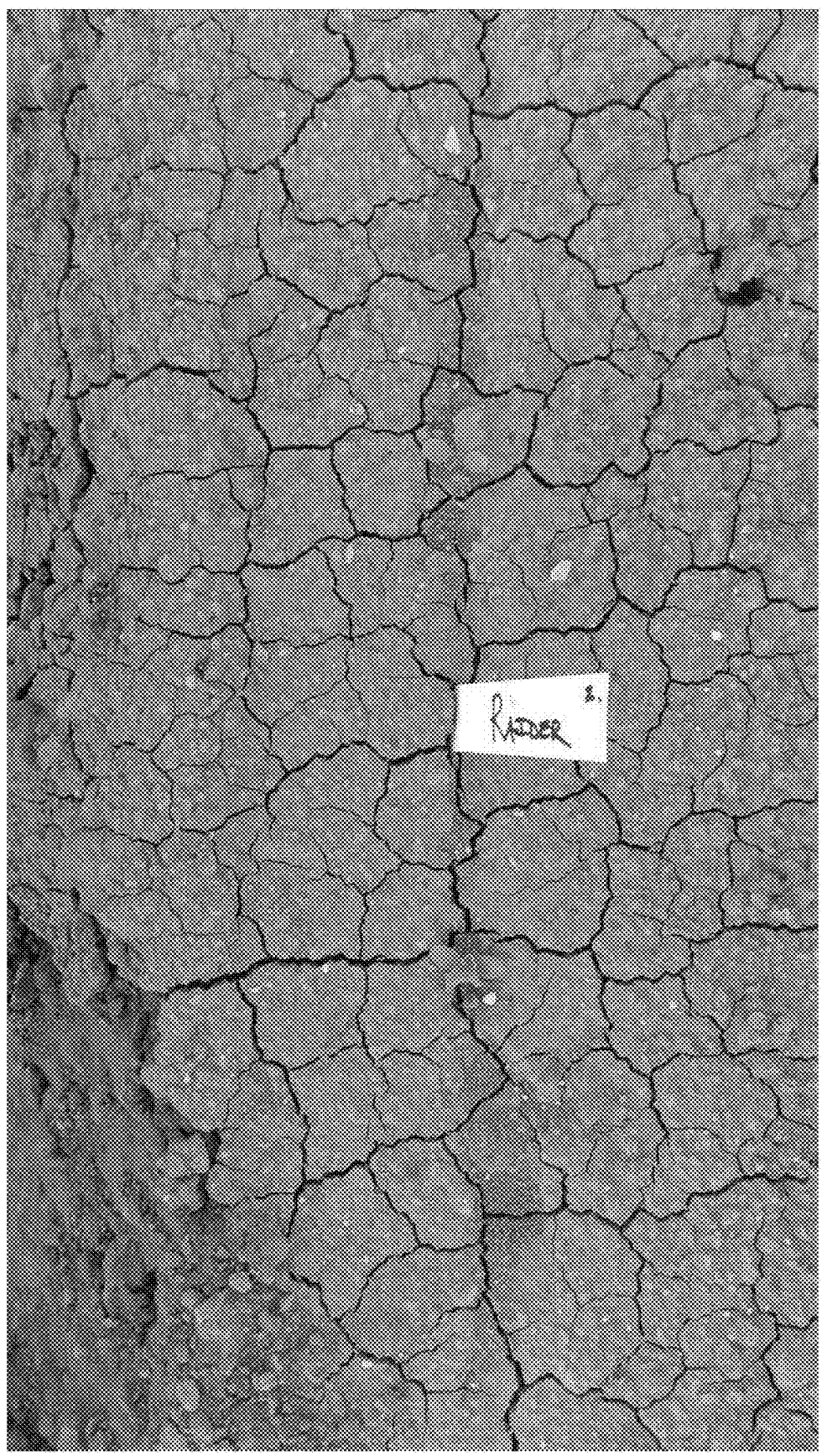
FIG. 4F shows seedlings of lettuce variety 'Raider'.
Figure 4G:
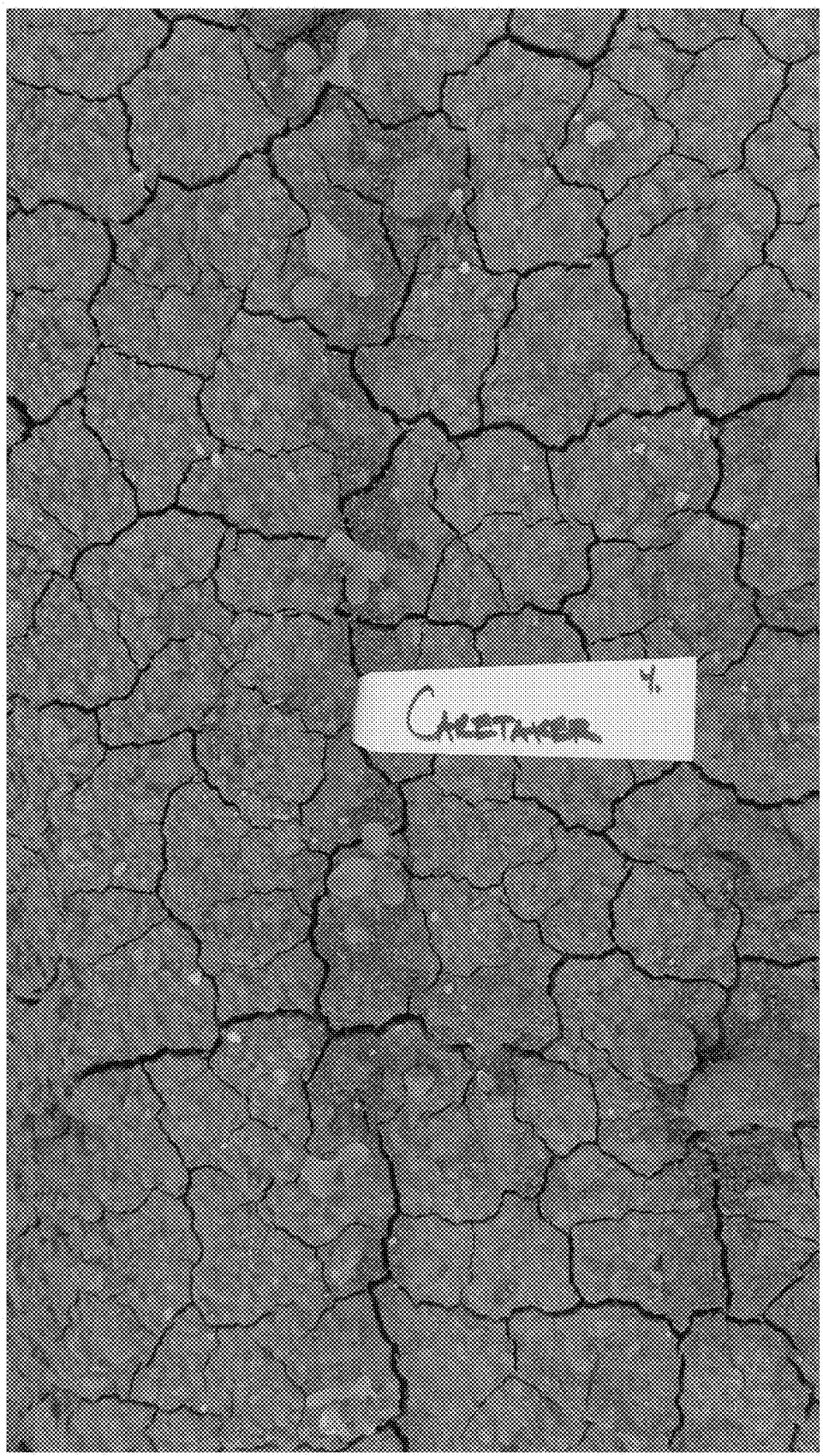
FIG. 4G shows seedlings of lettuce variety 'Caretaker'.
Figure 4H:
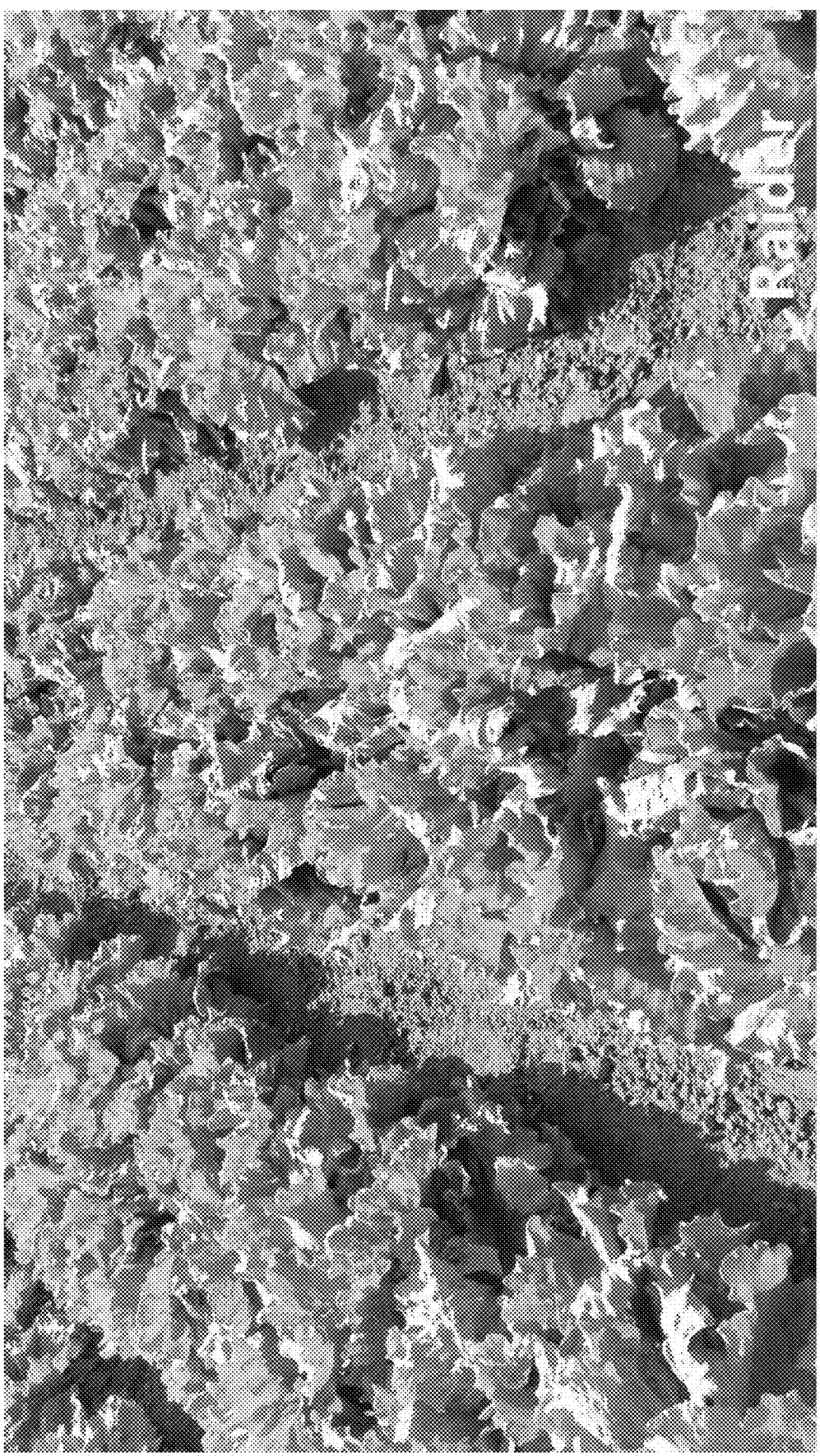
FIG. 4H shows plants of lettuce variety 'Raider'.
Figure 4I:
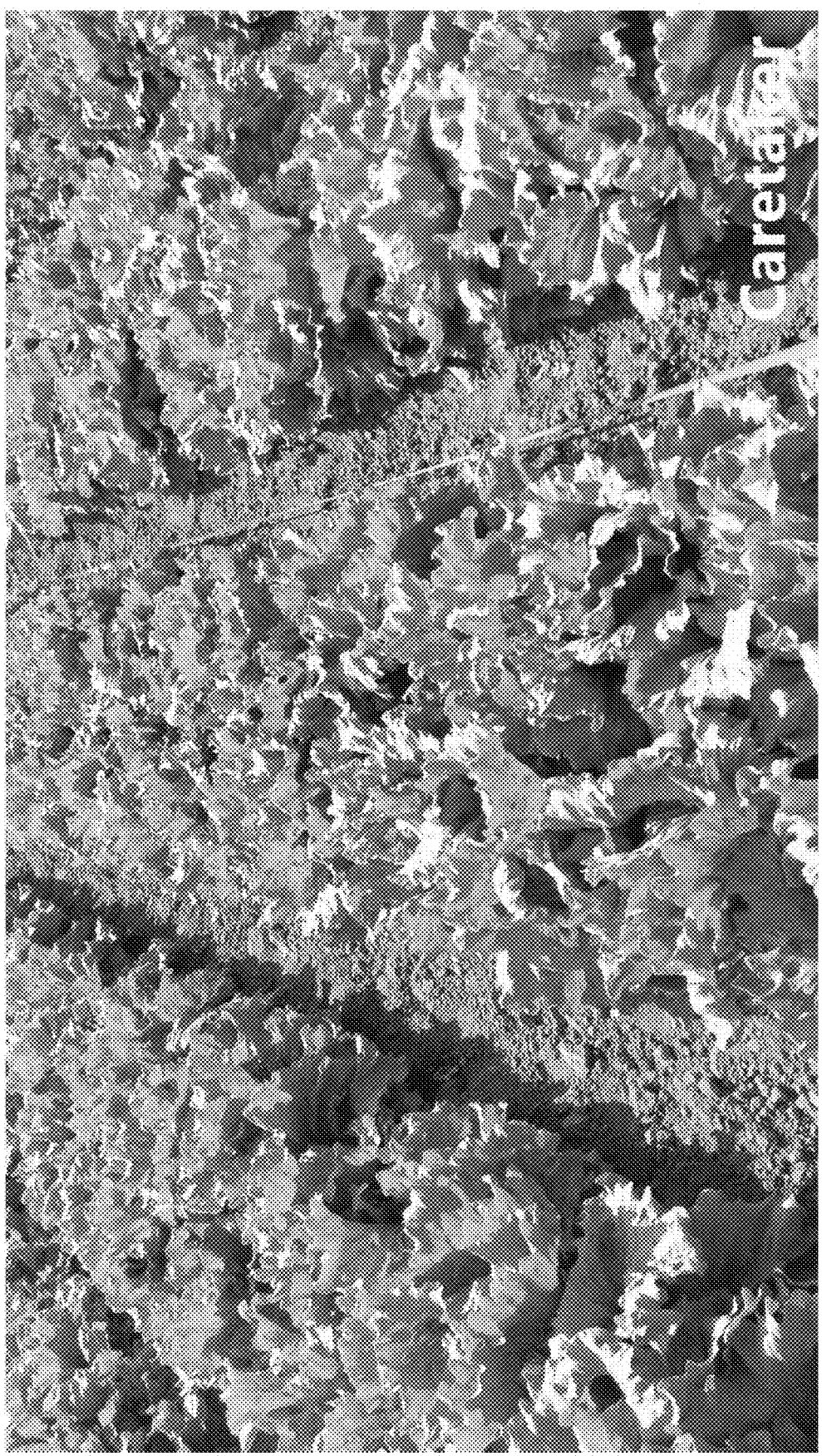
FIG. 4I shows plants of lettuce variety 'Caretaker'.
Figure 4J:
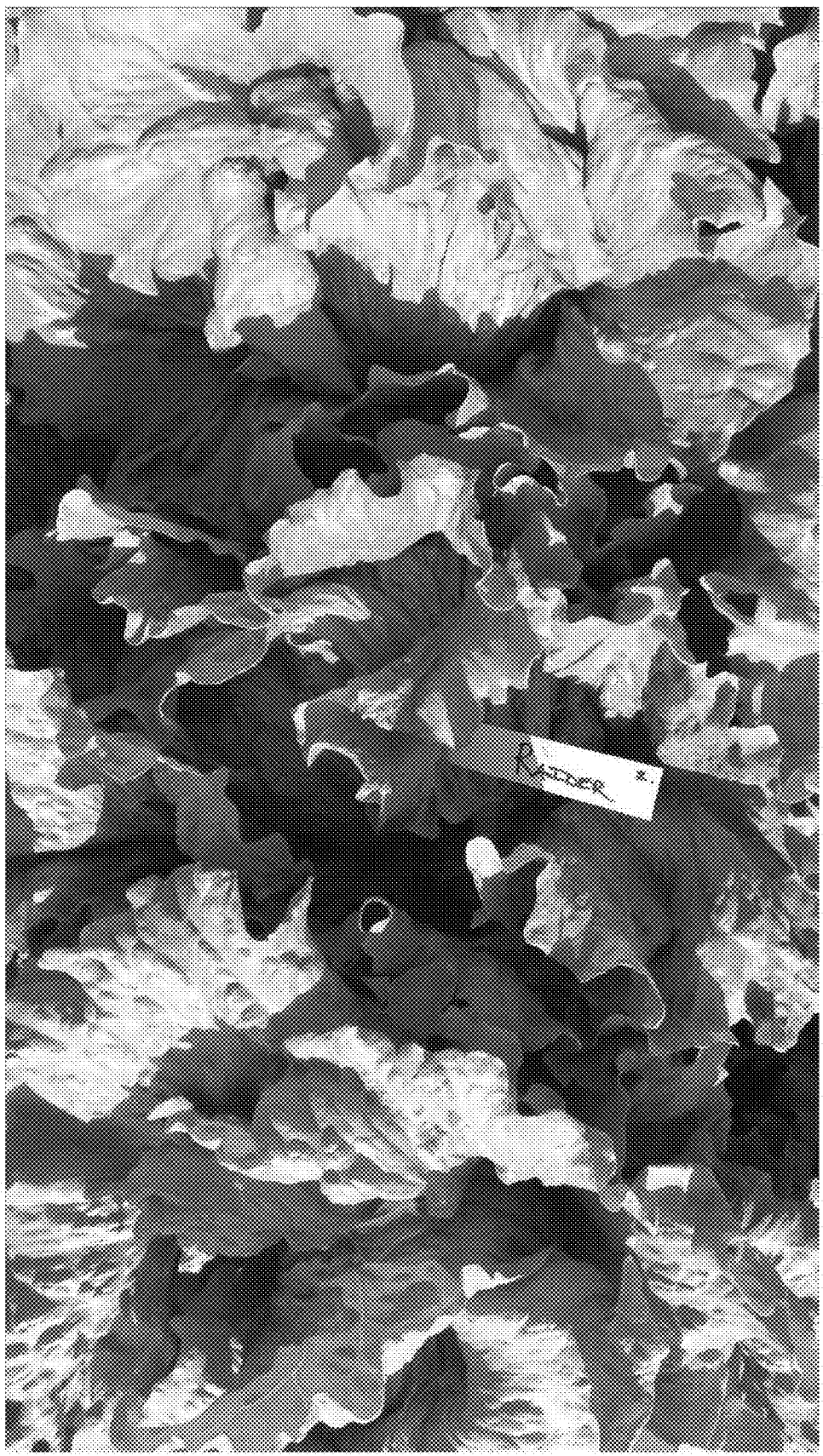
FIG. 4J shows a top view of a head of lettuce variety 'Raider'.
Figure 4K:
FIG. 4K shows a bottom view of a head of lettuce variety 'Raider'.
Figure 4L:
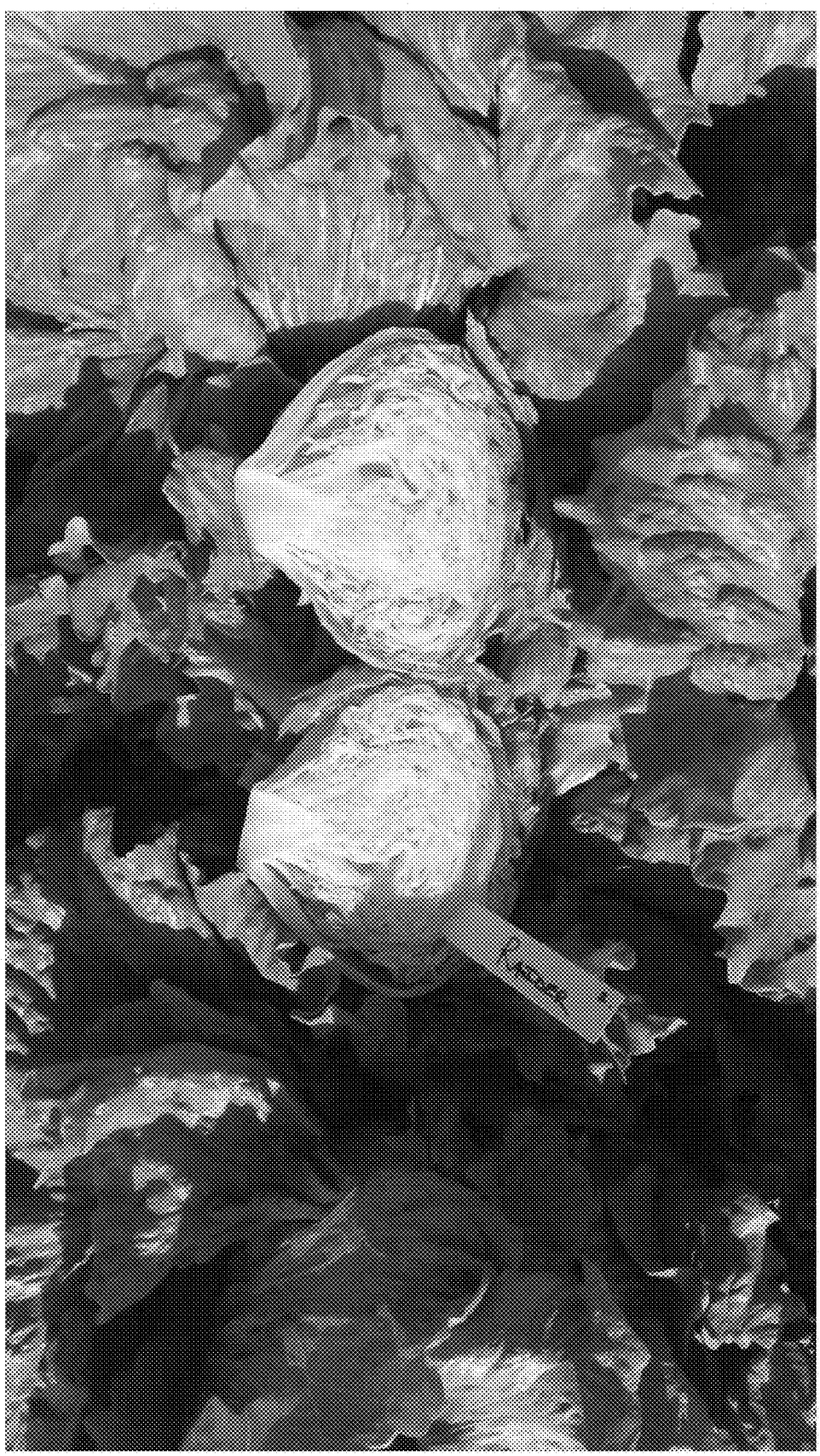
FIG. 4L shows a cross-sectional view of a head of lettuce variety 'Raider'.
Figure 4M:
FIG. 4M shows a top view of a head of lettuce variety 'Caretaker'.
Figure 4N:
FIG. 4N shows a bottom view of a head of lettuce variety 'Caretaker'.
Figure 4O:
FIG. 4O shows a cross-sectional view of a head of lettuce variety 'Caretaker'.
Figure 4P:
FIG. 4P shows a top view of heads of lettuce varieties 'Hotshot' (left) and 'Caretaker' (right).
Figure 4Q:
FIG. 4Q shows a top view of heads of lettuce varieties 'Hotshot' (left) and 'Raider' (right).
Figure 4R:
FIG. 4R shows a bottom view of heads of lettuce varieties 'Hotshot' (right) and 'Raider' (left).
Figure 4S:
FIG. 4S shows a bottom view of heads of lettuce varieties 'Hotshot' (right) and 'Caretaker' (left).
Figure 4T:
FIG. 4T shows a side view of heads of lettuce varieties 'Hotshot' (right) and 'Raider' (left).
Figure 4U:
FIG. 4U shows a side view of heads of lettuce varieties 'Hotshot' (right) and 'Caretaker' (left).
Figure 4V:
FIG. 4V shows a top view of heads of lettuce varieties 'Hotshot' (right) and 'Raider' (left).
Figure 4W:
FIG. 4W shows a top view of heads of lettuce varieties 'Hotshot' (right) and 'Caretaker' (left).
Figure 4X:
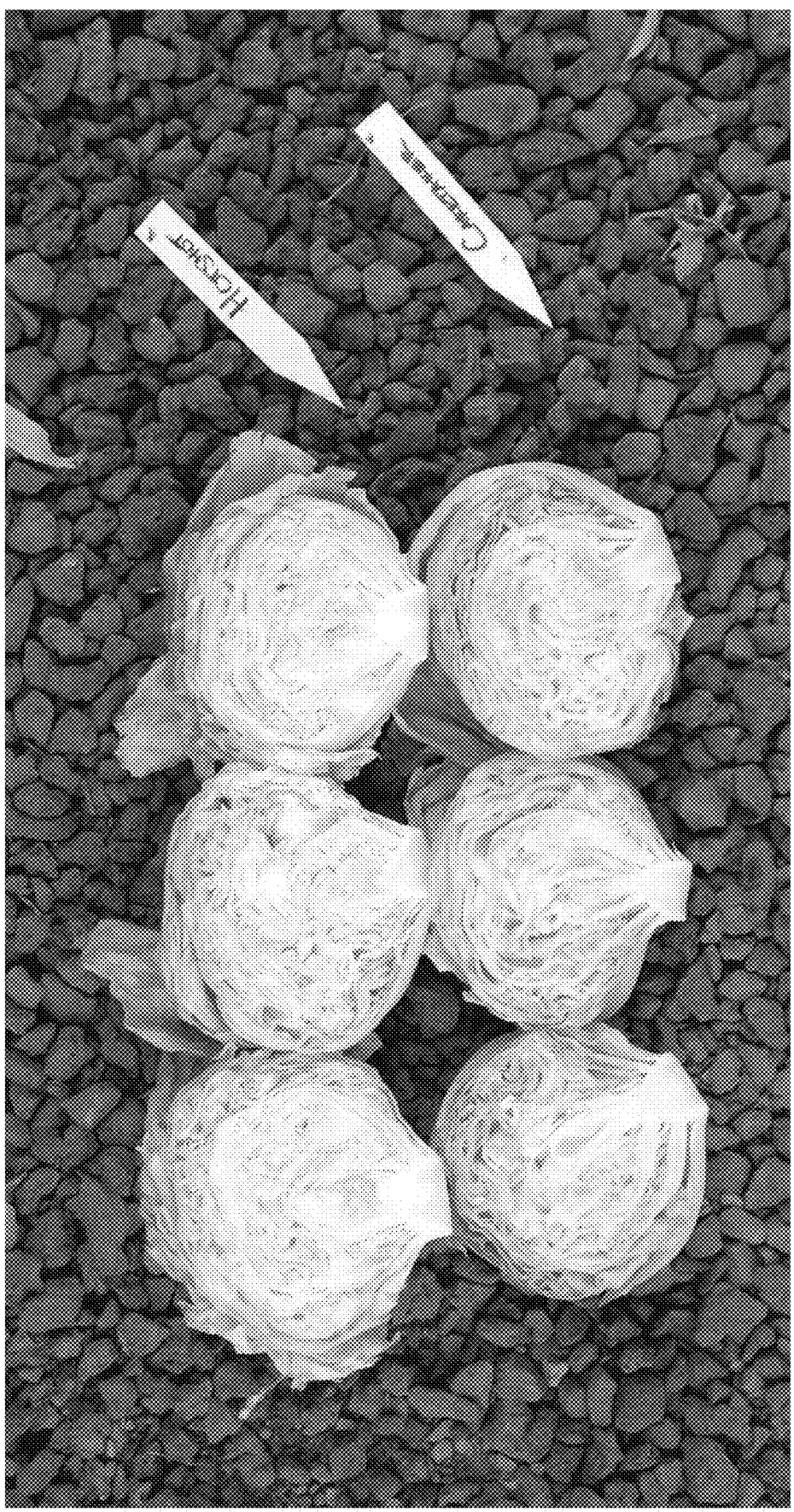
FIG. 4X shows a cross-sectional view of heads of lettuce varieties 'Hotshot' (top) and 'Caretaker' (bottom).
Figure 4Y:
FIG. 4Y shows a cross-sectional view of heads of lettuce varieties 'Hotshot' (top) and 'Raider' (bottom).
Figure 4Z:
FIG. 4Z shows a harvest-mature outer leaf of lettuce variety 'Raider'.
Figure 4A:
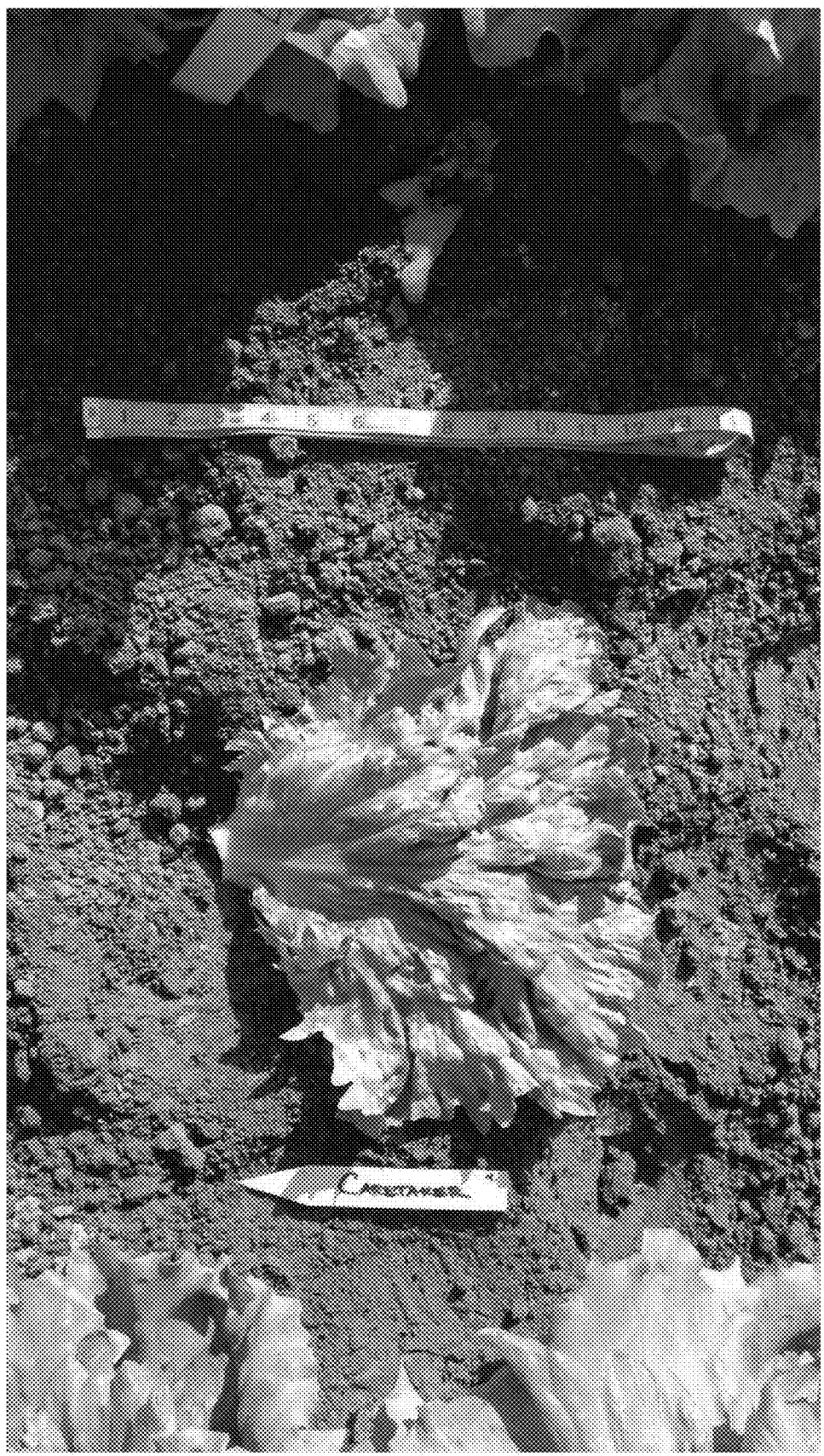
Figure 5A:
FIGS. 5A-5E show lettuce variety 'Uppercut'.
Figure 5B:
Figure 5C:
Figure 5D:
Figure 5E:

Further distinguishing features are apparent from the comparison of the varieties 'Hotshot', 'El Guapo', 'Caretaker', and 'Raider' depicted in FIGS. 4A-4AA.

Objective Description of the Variety 'Uppercut'

'Uppercut' is an open-pollinated iceberg lettuce variety. This variety is distinct and unique to all other iceberg lettuce varieties due to its earlier maturing time, larger frame, larger head diameter, and increased weight. Moreover, 'Uppercut' has a growing season that includes winter, spring, and summer, is suitable for cultivation in the open, and is adapted to growing in regions in the Southwest, such the Arizona desert, as well as the West Coast regions of the United States. FIGS. 5A-5E depict heads and plants of lettuce variety 'Uppercut'. Lettuce variety 'Uppercut' is the result of numerous generations of plant selections chosen for its resistance to *Fusarium* Wilt race 1.

The variety has shown uniformity and stability for the traits, within the limits of environmental influence for the traits. It has been self-pollinated a sufficient number of generations with careful attention to uniformity of plant type. The line has been increased with continued observation for uniformity. No variant traits have been observed or are expected in variety 'Uppercut'.

Lettuce variety 'Uppercut' has the following morphologic and other characteristics:

Plant type: Crisp (i.e., iceberg)
Seed:
  Color: Munsell 5YR 4/2 (Black)
  Seed light dormancy: Light not required
  Heat dormancy: Susceptible
Cotyledon to Fourth Leaf Stage:
  Shape of cotyledons: Spatulate
  Shape of fourth leaf: Elongated
  Apical margin: Finely dentate
  Basal margin: Moderately dentate
  Green color: Medium green
  Anthocyanin distribution: Absent
  Cupping: Slight Reflexing: Apical margin
Mature Leaves:
Margin:
Incision depth: Moderate
Indentation: Crenate
Undulation of apical margin: Moderate
Green color: Munsell 5GY 5/8 (Medium green)
Anthocyanin distribution: Absent
Leaf glossiness: Dull
Blistering: Moderate
Leaf thickness: Thick
Trichomes: Absent (smooth)
Plant:
Spread of frame leaves: 49.8 cm
Head diameter (market trimmed with single cap leaf): 14.5 cm
Head shape: Spherical
Head size class: Large
Head firmness: Firm
Butt:
Butt shape: Rounded
Midrib: Moderately raised
Core:
Core diameter at base of head: 32.3 mm
Ratio of head diameter/core diameter: 4.5
Core height from base of head to apex: 37.1 mm
Bolting:
Number of days from first water to seed stalk emergence under summer conditions: 69 days
Bolting class: Medium
Mature seed stalk height: 127.4 cm
Mature seed stalk spread: 46 cm
Spread of bolter plant at widest point: 33.9 cm
Bolter leaves: Curved
Margin: Entire
Bolter habit:
Terminal inflorescence: Present
Lateral shoots: Present
Basal side shoots: Absent
Disease Resistance:
Downy Mildew (*Bremia lactucae*) (Bl): Susceptible to Bl:16-18, Bl:20-27, Bl:29-Bl:31, and Bl:33
Lettuce mosaic virus (LMV) strain Ls-1: Susceptible
*Fusarium* Wilt (*Fusarium oxysporum* f. sp. *lactucae*) race 1: Resistant
Big Vein Virus: Susceptible
Powdery Mildew: Susceptible
Corky Root Rot: Susceptible
Pest Resistance:
*Nasonovia ribisnigri* biotype 0 (Nr:0): Susceptible
Stress Resistance:
Tipburn: Moderately resistant/moderately susceptible
Heat: Susceptible
Cold: Susceptible
Pink rib: Moderately resistant/moderately susceptible
Rusty brown discoloration: Moderately resistant/moderately susceptible
Internal rib necrosis: Moderately resistant/moderately susceptible
Comparisons to Other Lettuce Variety Table 5A below compares characteristics of lettuce variety 'Uppercut' with the lettuce variety 'Headmaster' (PVP Certificate No. 9800023). Column 1 lists the characteristics, column 2 shows the characteristics for lettuce variety 'Uppercut', and column 3 shows the characteristics for lettuce variety 'Telluride'.

TABLE 5A

| Characteristic | 'Uppercut' | 'Headmaster' |
|---|---|---|
| Maturing time | Earlier maturing | Later maturing |
| Frame size | Larger frame | Smaller frame |
| Head diameter | Increased head diameter | Decreased head diameter |
| Rib smoothness | Smoother rib | Less smooth rib |
| Head weight | Increased weight | Decreased weight |

Table 5B below compares characteristics of lettuce variety 'Uppercut' with the lettuce variety 'Thunderhead' (PVP Certificate No. 201100043) and the lettuce variety 'Headmaster' (PVP Certificate No. 980023). Column 1 lists the characteristics, column 2 shows the characteristics for lettuce variety 'Uppercut', column 3 shows the characteristics for lettuce variety 'Thunderhead', and column 4 shows the characteristics for lettuce variety 'Headmaster'.

TABLE 5B

| Characteristic | 'Uppercut' | 'Thunderhead' | 'Headmaster' |
|---|---|---|---|
| Spread of frame leaves | 49.8 cm | 47.9 cm | 49.7 cm |
| Head weight | 684.6 g | 611.3 g | 501.7 g |
| Head diameter (market trimmed with single cap leaf) | 145.1 mm | 138.2 mm | 136.2 mm |
| Core diameter at base of head | 32.3 mm | 32.3 mm | 29.9 mm |
| Core height from base of head to apex | 37.1 mm | 32 mm | 24.6 mm |
| Ratio of head diameter/core diameter | 4.5 | 4.3 | 4.6 |
| Color of mature outer leaves (Munsell) | 5GY 5/8 | 5GY 5/8 | 5GY 4/8 |

Tables 6A-6C below show results of a first trial that compares the head weight, head diameter, core length, core diameter, and frame diameter of 20 plants of the lettuce variety 'Uppercut' (Table 6A) with those of 20 plants of lettuce variety 'Thunderhead' (Table 6B) and 20 plants of variety 'Headmaster' (Table 6C).

TABLE 6A

| 'Uppercut' | Head Wt. | Head Diameter | Core Length | Core Diameter | Frame Diameter |
|---|---|---|---|---|---|
| Max | 905 g | 164 mm | 47 mm | 39 mm | 61 cm |
| Min | 550 g | 138 mm | 25 mm | 32 mm | 51 cm |
| Average | 733.75 g | 150.95 mm | 36.05 mm | 35.25 mm | 55.2 cm |
| Std. Dev | 116.58 | 8.99 | 5.17 | 1.71 | 2.49 |

TABLE 6B

| 'Thunderhead' | Head Wt. | Head Diameter | Core Length | Core Diameter | Frame Diameter |
|---|---|---|---|---|---|
| Max | 860 g | 167 mm | 35 mm | 41 mm | 59 cm |
| Min | 395 g | 110 mm | 23 mm | 30 mm | 45.5 cm |
| Average | 582.5 g | 140.2 mm | 28.25 mm | 34.3 mm | 52.9 cm |
| Std. Dev | 114.38 | 13.63 | 2.92 | 2.43 | 3.20 |

TABLE 6C

| 'Headmaster' | Head Wt. | Head Diameter | Core Length | Core Diameter | Frame Diameter |
|---|---|---|---|---|---|
| Max | 720 g | 169 mm | 31 mm | 36 mm | 59.5 cm |
| Min | 470 g | 123 mm | 23 mm | 27 mm | 48.5 cm |
| Average | 570.05 g | 144.95 mm | 25.8 mm | 32.65 mm | 53.375 cm |
| Std. Dev | 74.04 | 14.04 | 2.57 | 2.13 | 2.64 |

Tables 6D-6F below show results of a second trial that compares the head weight, head diameter, core length, core diameter, and frame diameter of 20 plants of the lettuce variety 'Uppercut' (Table 6D) with those of 20 plants of lettuce variety 'Thunderhead' (Table 6E) and 20 plants of variety 'Headmaster' (Table 6F).

TABLE 6D

| 'Uppercut' | Head Wt. | Head Diameter | Core Length | Core Diameter | Frame Diameter |
|---|---|---|---|---|---|
| Max | 830 g | 155 mm | 48 mm | 34 mm | 46 cm |
| Min | 380 g | 111 mm | 28 mm | 26 mm | 43 cm |
| Average | 635.5 g | 139.3 mm | 38.2 mm | 29.35 mm | 44.325 cm |
| Std. Dev | 113.81 | 10.51 | 5.56 | 2.01 | 1.00 |

TABLE 6E

| 'Thunderhead' | Head Wt. | Head Diameter | Core Length | Core Diameter | Frame Diameter |
|---|---|---|---|---|---|
| Max | 825 g | 150 mm | 45 mm | 35 mm | 46 cm |
| Min | 485 g | 125 mm | 25 mm | 26 mm | 40 cm |
| Average | 640 g | 136.15 mm | 35.75 mm | 30.3 mm | 43.025 cm |
| Std. Dev | 103.83 | 6.96 | 5.85 | 2.56 | 1.63 |

TABLE 6F

| 'Headmaster' | Head Wt. | Head Diameter | Core Length | Core Diameter | Frame Diameter |
|---|---|---|---|---|---|
| Max | 610 g | 155 mm | 39 mm | 31 mm | 48 cm |
| Min | 245 g | 105 mm | 18 mm | 21 mm | 44 cm |
| Average | 433.25 g | 127.45 mm | 23.3 mm | 27.25 mm | 46.075 cm |
| Std. Dev | 103.91 | 14.48 | 4.50 | 2.63 | 1.15 |

Figure 6A:
FIGS. 6A-6R show comparisons between lettuce varieties 'Uppercut', 'Headmaster', and 'Thunderhead'.
Figure 6B:
FIG. 6B show plants of lettuce variety 'Thunderhead'.
Figure 6C:
FIG. 6C shows a top view of a head of lettuce variety 'Thunderhead'.
Figure 6D:
FIG. 6D shows a bottom view of a head of lettuce variety 'Thunderhead'.
Figure 6E:
FIG. 6E shows a cross-sectional view of a head of lettuce variety 'Thunderhead'.
Figure 6F:
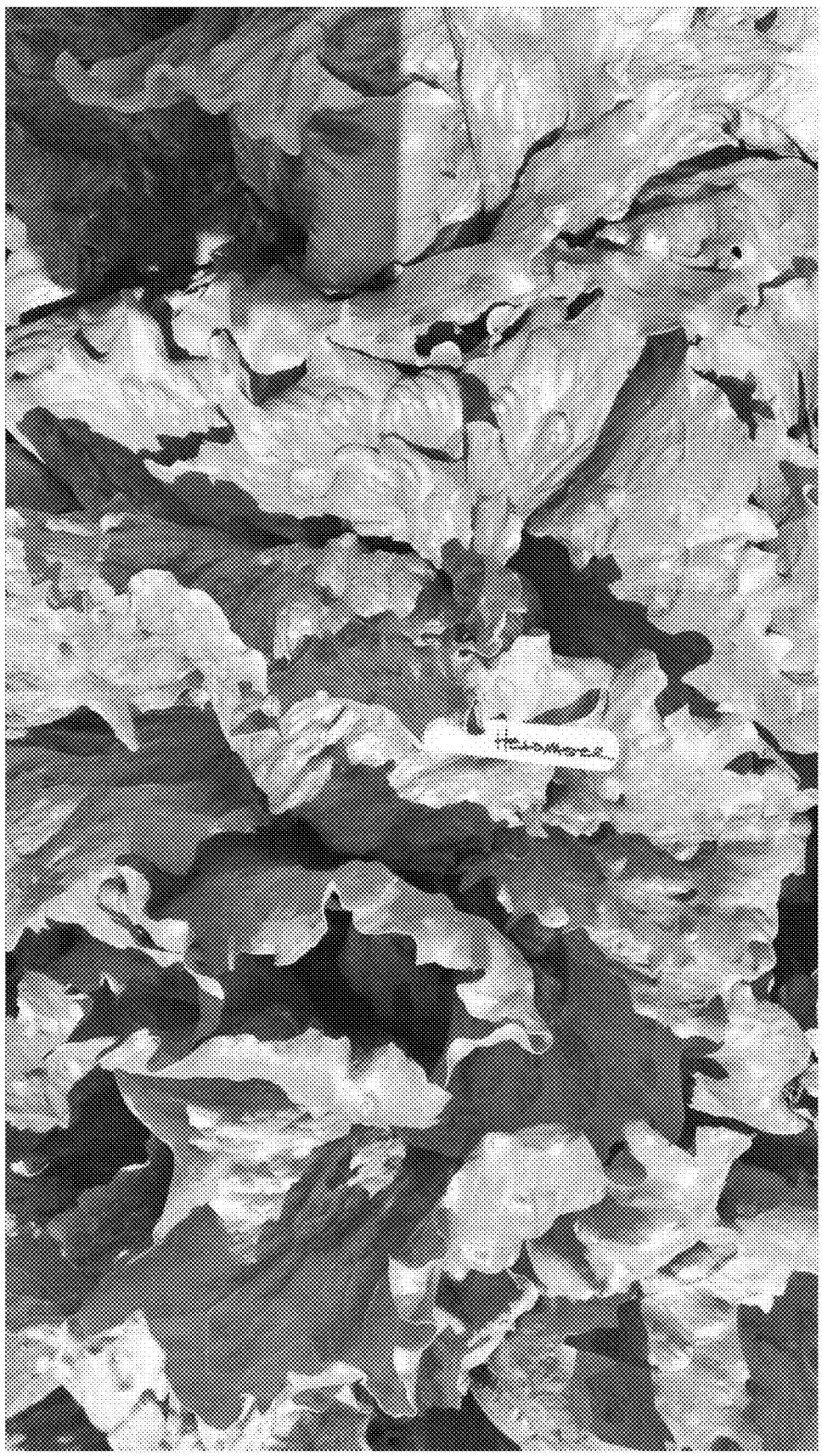
FIG. 6F shows a top view of a head of lettuce variety 'Headmaster'.
Figure 6G:
FIG. 6G shows a bottom view of a head of lettuce variety 'Headmaster'.
Figure 6H:
FIG. 6H shows a cross-sectional view of a head of lettuce variety 'Headmaster'.
Figure 6I:
FIG. 6I shows a top view of heads of lettuce varieties 'Thunderhead' (top) and 'Uppercut' (bottom).
Figure 6J:
FIG. 6J shows a top view of heads of lettuce varieties 'Headmaster' (top) and 'Uppercut' (bottom).
Figure 6K:
FIG. 6K shows a bottom view of heads of lettuce varieties 'Thunderhead' (top) and 'Uppercut' (bottom).
Figure 6L:
FIG. 6L shows a bottom view of heads of lettuce varieties 'Headmaster' (top) and 'Uppercut' (bottom).
Figure 6M:
FIG. 6M shows a side view of heads of lettuce varieties 'Thunderhead' (top) and 'Uppercut' (bottom).
Figure 6N:
FIG. 6N shows a side view of heads of lettuce varieties 'Headmaster' (top) and 'Uppercut' (bottom).
Figure 60:
Figure 6P:
FIG. 6P shows a cross-sectional view of heads of lettuce varieties 'Headmaster' (left) and 'Uppercut' (right).
Figure 6Q:
FIG. 6Q shows harvest-mature outer leaves of lettuce varieties 'Thunderhead' (top) and 'Uppercut' (bottom).
Figure 6R:

Further distinguishing features are apparent from the comparison of the varieties 'Uppercut', 'Thunderhead', and 'Headmaster', depicted in FIGS. 6A-6R.

Further Embodiments

Breeding

In lettuce breeding, lines are selected for their appropriate characteristics. For example, one line may be selected for bolt tolerance in the fall growing conditions of the desert production locations of California and Arizona. Another line may be selected for the size, color, and texture of the lettuce head. Crosses are made, for example, to produce a dark green, sure heading iceberg lettuce with improved texture, and size for fall plantings in Yuma, Ariz. and the Salinas Valley, Calif.

To optimize crossing, it is important to note that lettuce is an obligate self-pollinating species. This means that the pollen is shed before stigma emergence, assuring 100% self-fertilization. Since each lettuce flower is an aggregate of about 10-20 individual florets (typical of the Compositae family), manual removal of the anther tubes containing the pollen is performed by procedures well known in the art of lettuce breeding.

The manual removal of anther tubes, though an effective means to ensure the removal of all self pollinating possi bilities, is very tedious and time consuming when a large number of crosses are to be made. The breeders have therefore adapted a well documented and modified method of making crosses more efficiently using these methods. This particular cross was made by first misting the designated male flowers to wash the pollen off prior to fertilization. This process of misting is a proven and effective means of pollen removal that assures crossing or hybridization. About 60-90 minutes past sunrise, flowers to be used for crossings are selected. The basis for selection are open flowers, with the stigma emerged and the pollen visibly attached to the single stigma (about 10-20 stigma). Using 3-4 pumps of water from a regular spray bottle, the pollen is washed off with enough pressure to dislodge the pollen grains, but not enough to damage the style. Excess water is dried off with clean paper towels. About 30 minutes later, the styles should spring back up and the two lobes of the stigma are visibly open in a "V" shape. Pollen from another variety or donor parent is then introduced by gently rubbing the stigma and style of the donor parent to the maternal parent. Tags with the pertinent information on date and pedigree are then secured to the flowers in order to keep track.

About 2-3 weeks after pollination, seeds are harvested when the involucre have matured. The seeds are eventually sown and in the presence of markers such as leaf color or leaf margins, the selfed or maternal seedlings or plants are identified. Generally, there are no visible markers and breeders must wait until the $F_2$ generations when expected segregation patterns for the genetic character of interest can be followed. This latter situation mandates a lengthy wait to determine if hybrids are produced. Two relevant references teaching methods for out crossing lettuce are: (1) Ryder, E. J. and A. S. Johnson. 1974. Mist depollination of lettuce flowers. Hortscience 9:584; and (2) Nagata, R. T. 1992. Clip and Wash Method of Emasculation for Lettuce. Hortscience 27(8):907-908 both of which are hereby incorporated by reference in their entirety for the purpose of providing details on the techniques well known in the art.

Selection

In addition to crossing, selection may be used to identify and isolate new lettuce lines. In lettuce selection, lettuce seeds are planted, the plants are grown and single plant selections are made of plants with desired characteristics. Such characteristics may include improved head and frame size, deeper or darker green leaf color, etc. Seed from the single plant selections are harvested, separated from seeds of the other plants in the field and re-planted. The plants from the selected seed are monitored to determine if they exhibit the desired characteristics of the originally selected line. Selection work is continued over multiple generations to increase the uniformity of the new line.

DEPOSIT INFORMATION

Lettuce Variety 'Hotshot'

A deposit of the lettuce variety 'Hotshot' is maintained by Pinnacle Seed, Inc., having an address of P.O. Box 222672, Carmel, Calif. 93923, United States of America. Access to this deposit will be available during the pendency of this application to persons determined by the Commissioner of Patents and Trademarks to be entitled thereto under 37 C.F.R. § 1.14 and 35 U.S.C. § 122. Upon allowance of any claims in this application, all restrictions on the availability to the public of the variety will be irrevocably removed by affording access to a deposit of at least 2,500 seeds of the same variety made according to the Budapest Treaty in the American Type Culture Collection, (ATCC), ATCC Patent Depository, 10801 University Boulevard, Manassas, Va., 20110, USA.

The lettuce variety 'Hotshot' was deposited on Nov. 1, 2021 according to the Budapest Treaty in the American Type Culture Collection (ATCC), ATCC Patent Depository, 10801 University Boulevard, Manassas, Va., 20110, USA. The deposit has been assigned ATCC number PTA-127155. Access to this deposit will be available during the pendency of this application to persons determined by the Commissioner of Patents and Trademarks to be entitled thereto under 37 C.F.R. § 1.14 and 35 U.S.C. § 122. Upon allowance of any claims in this application, all restrictions on the availability to the public of the variety will be irrevocably removed.

The deposit will be maintained in the ATCC depository, which is a public depository, for a period of at least 30 years, or at least 5 years after the most recent request for a sample of the deposit, or for the effective life of the patent, whichever is longer, and will be replaced if a deposit becomes nonviable during that period.

What is claimed:

1. A *Lactuca sativa* seed designated as 'Hotshot', representative sample of seed having been deposited under ATCC Accession Number PTA-127155.

2. A *Lactuca sativa* plant produced by growing the seed of claim 1.

3. A plant part from the plant of claim 2.

4. The plant part of claim 3, wherein said part is a head, a leaf, or a portion thereof.

5. The plant part of claim 4, wherein said part is a head.

6. A *Lactuca sativa* plant having all the physiological and morphological characteristics of the *Lactuca sativa* plant of claim 2.

7. A plant part from the plant of claim 6.

8. The plant part of claim 7, wherein said part is a head, a leaf, or a portion thereof.

9. The plant part of claim 8, wherein said part is a head.

10. An $F_1$ hybrid *Lactuca sativa* plant having 'Hotshot' as a parent where 'Hotshot' is grown from the seed of claim 1.

11. A pollen grain or an ovule of the plant of claim 2.

12. A tissue culture of the plant of claim 2.

13. A *Lactuca sativa* plant regenerated from the tissue culture of claim 12, wherein
   the plant has all of the morphological and physiological characteristics of a lettuce plant produced by growing seed designated as 'Hotshot', representative sample of seed having been deposited under ATCC Accession Number PTA-127155.

14. A method of making *Lactuca sativa* seeds, said method comprising crossing the plant of claim 2 with another lettuce plant and harvesting seed therefrom.

15. A method of selecting *Lactuca sativa*, comprising:
   a) growing more than one plant from the seed of claim 1; and
   b) selecting a plant from step a).

* * * * *